United States Patent
Gardiner et al.

[19]

[11] Patent Number: 6,074,401

[45] Date of Patent: *Jun. 13, 2000

[54] PINNED RETAINER SURGICAL FASTENERS, INSTRUMENTS AND METHODS FOR MINIMALLY INVASIVE VASCULAR AND ENDOSCOPIC SURGERY

[75] Inventors: Barry N. Gardiner, Orinda; Paul T. McDonald, Oakland; Richard D. Phipps, Morgan Hill, all of Calif.

[73] Assignee: Coalescent Surgical, Inc., Sunnyvale, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/781,578

[22] Filed: Jan. 9, 1997

[51] Int. Cl.$^7$ ...................................................... A61B 17/10

[52] U.S. Cl. ............................................................. 606/139

[58] Field of Search .................................. 606/139, 144, 606/151, 147, 232

[56] References Cited

U.S. PATENT DOCUMENTS

| | | | |
|---|---|---|---|
| 2,413,142 | 12/1946 | Jones et al. | 606/232 |
| 5,855,614 | 1/1999 | Stevens et al. | 623/11 |
| 5,879,371 | 3/1999 | Gardiner et al. | 606/224 |

*Primary Examiner*—Gary Jackson
*Assistant Examiner*—Daphna Shai
*Attorney, Agent, or Firm*—Morrison & Foerster LLP

[57] ABSTRACT

A surgical fastener in the form of a pinned retainer, instrument and method are provided for constructing a graft to artery anastomosis and other soft tissue anastomoses, particularly by minimally invasive (or endoscopic) surgery. The pinned retainer fastener is comprised of a needle and a retainer. The needle has a base, shaft and tip that allow this member to be sewn through, for example, a graft and artery to be joined. The retainer has an aperture to receive and securely engage the needle shaft to seal the graft and artery together between cooperating surfaces of the needle base and retainer. The instrument holds the needle and retainer at its distal or working end, and controls in the handle allow application of the retainer. The method employs the pinned retainer fasteners and instrument to join soft tissues and to construct graft to artery anastomoses.

37 Claims, 9 Drawing Sheets

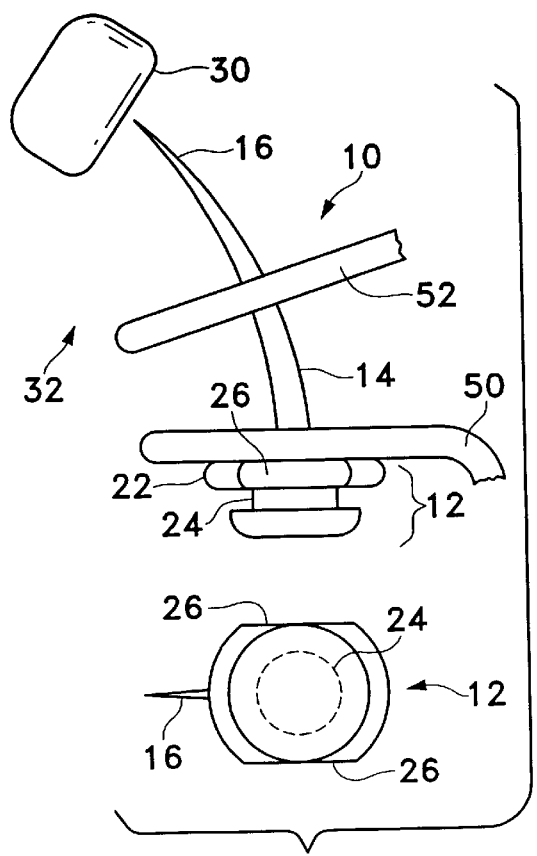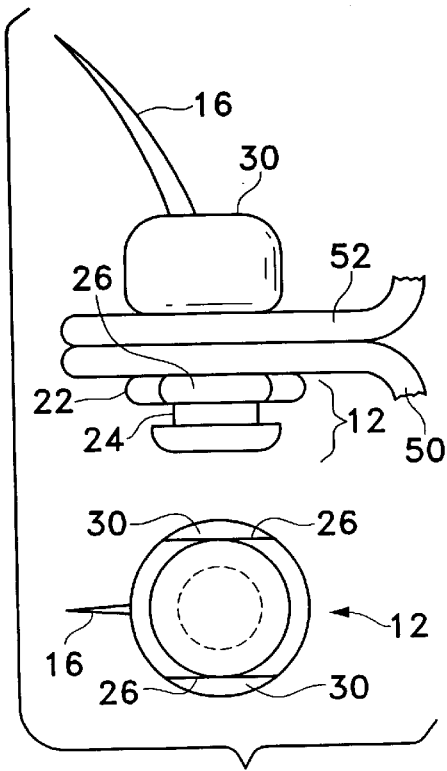
FIG. 1A  FIG. 1B
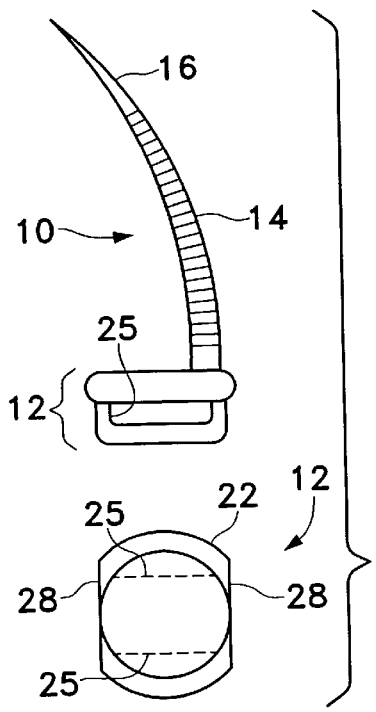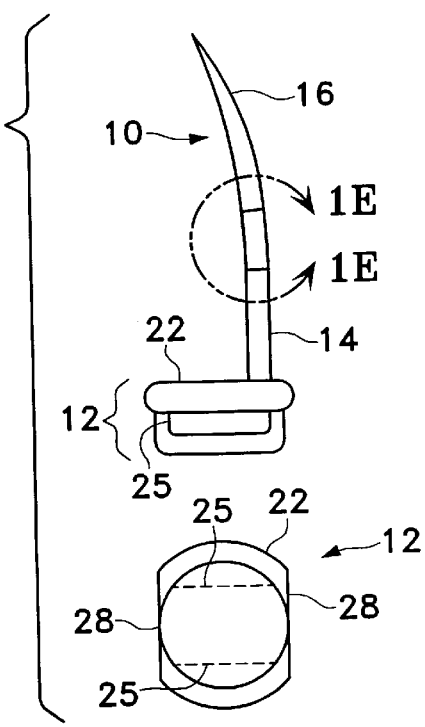
FIG. 1C  FIG. 1D
FIG. 1E

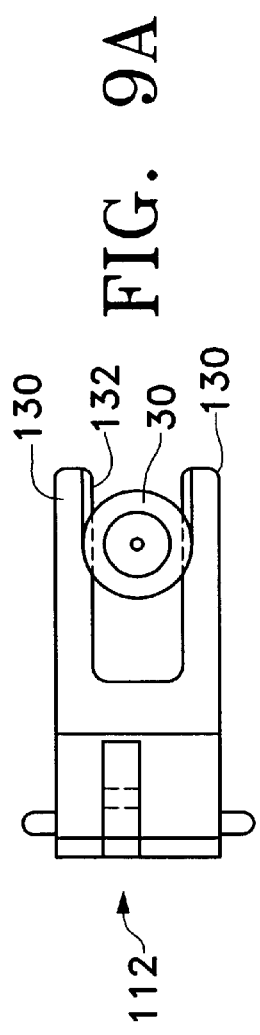
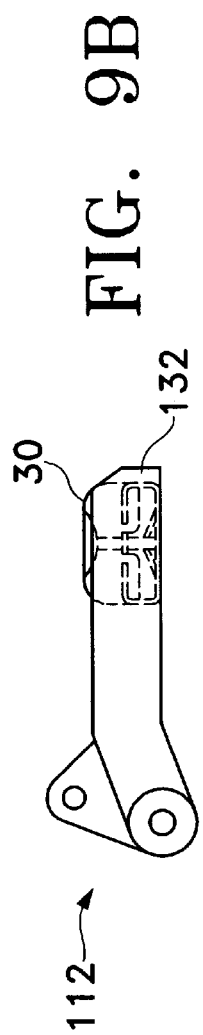
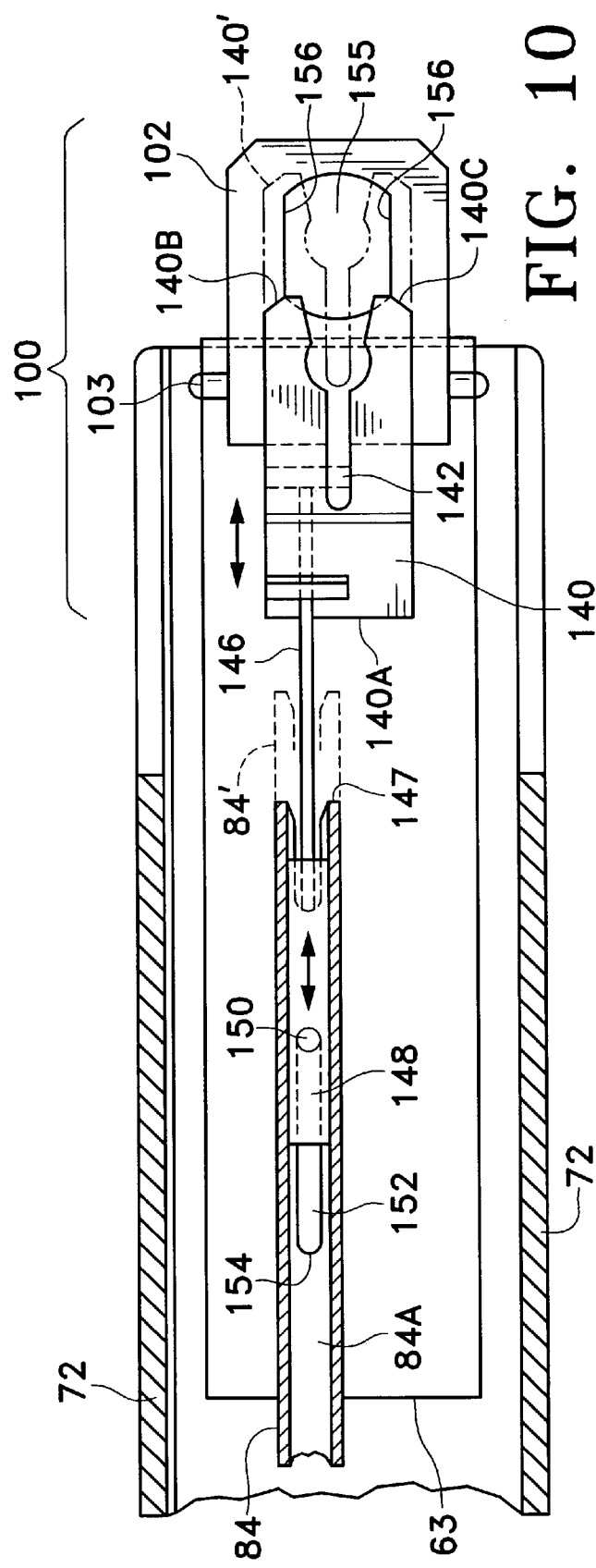

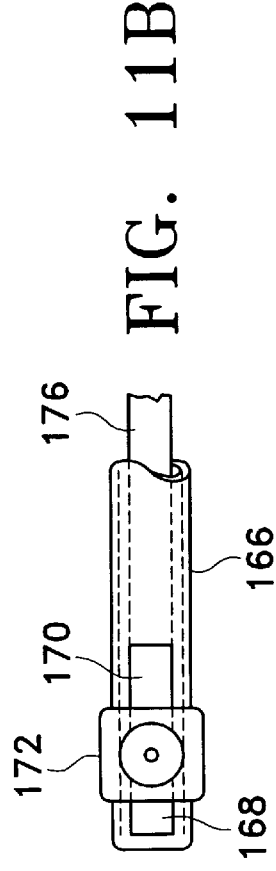
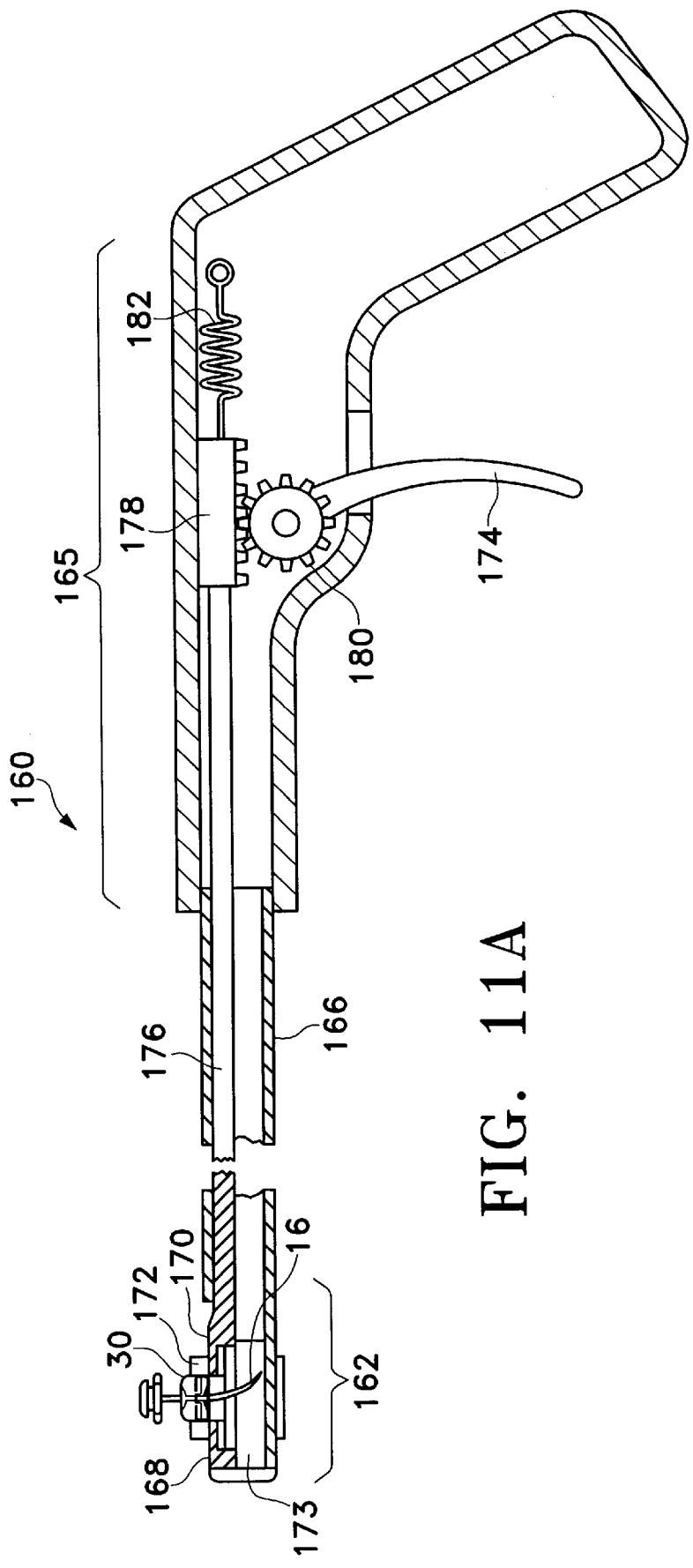
FIG. 11B
FIG. 11A

PINNED RETAINER SURGICAL FASTENERS, INSTRUMENTS AND METHODS FOR MINIMALLY INVASIVE VASCULAR AND ENDOSCOPIC SURGERY

BACKGROUND OF THE INVENTION

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trochar, which is a pointed, piercing device, is delivered into the body with a cannula. After the trochar pierces the abdominal or thoracic wall, it is removed and the cannula is left with one end in the body cavity, where the operation is to take place, and the other end opening to the outside. A cannula has a small inside diameter, typically 5–10 millimeters, and sometimes up to as much as 20 millimeters. A number of such cannulas are inserted for any given operation.

A viewing instrument, typically including a miniaturized video camera, is inserted through one of these cannulas and a variety of surgical instruments and retractors are inserted through others. The image provided by the viewing device may be displayed on a video screen or television monitor, affording the surgeon enhanced visual control over the instruments. Because a commonly used viewing instrument is called an "endoscope," this type of surgery is often referred to as "endoscopic surgery." In the abdomen, endoscopic procedures are commonly referred to as laparoscopic surgery, and in the chest, as thoracoscopic surgery. Abdominal procedures may take place either inside the abdominal cavity (in the intraperitoneal space) or in a space created behind the abdominal cavity (in the retroperitoneal space). The retroperitoneal space is particularly useful for operations on the aorta and spine.

Minimally invasive surgery has virtually replaced open surgical techniques for operations such as cholecystectomy and anti-reflux surgery of the esophagus and stomach. This has not occurred in either peripheral vascular surgery or cardiovascular surgery. An important type of vascular surgery is to replace or bypass a diseased, occluded or injured artery. Arterial replacement or bypass grafting has been performed for many years using open surgical techniques and a variety of prosthetic grafts. These grafts are manufactured as fabrics (often from Dacron or Teflon) or are prepared as autografts (from the patient's own tissues) or heterografts (from the tissues of animals). A graft can be joined to the involved artery in a number of different positions, including end-to-end, end-to-side, and side-to-side. This attachment between artery and graft is known as an anastomosis. Constructing an arterial anastomosis is technically challenging for a surgeon in open surgical procedures, and is almost a technical impossibility using minimally invasive techniques.

Many factors contribute to the difficulty of performing arterial replacement or bypass grafting. See generally, Wylie, Edwin J. et al., Manual of Vascular Surgery, (Springer-Verlag New York), 1980. One such factor is that the tissues to be joined must be precisely aligned with respect to each other to ensure the integrity and patency of the anastomosis. If one of the tissues is affixed too close to its edge, the suture can rip through the tissue and impair both the tissue and the anastomosis. Conversely, if the tissues are joined too far from their edges, it can significantly narrow the size of the anastomosis. Another factor is that, even after the tissues are properly aligned, it is difficult and time consuming to pass the needle through the tissues, form the knot in the suture material, and ensure that the suture material does not become tangled. These difficulties are exacerbated by the small size of the artery and graft. The arteries subject to peripheral vascular and cardiovascular surgery typically range in diameter from several millimeters to several centimeters. A graft is typically about the same size as the artery to which it is being attached. Another factor contributing to the difficulty of such procedures is the limited time available to complete the procedure. The time the surgeon has to complete an arterial replacement or bypass graft is limited because there is no blood flowing through the artery while the procedure is being done. If blood flow is not promptly restored, sometimes in as little as thirty minutes, the tissue the artery supplies may experience significant damage, or even death (tissue necrosis). In addition, arterial replacement or bypass grafting is made more difficult by the need to accurately place and space many sutures to achieve a permanent hemostatic seal. Precise placement and spacing of sutures is also required to achieve an anastomosis with long-term patency.

Highly trained and experienced surgeons are able to perform arterial replacement and bypass grafting in open surgery using conventional sutures and suturing techniques. A suture has a suture needle that is attached or "swedged on" to a long, trailing suture material. The needle must be precisely controlled and accurately placed through both graft and artery. The trailing suture material must be held with proper tension to keep the graft and artery together, and must be carefully manipulated to prevent the suture material from tangling. In open surgery, these maneuvers can usually be accomplished within the necessary time frame, thus avoiding the subsequent tissue damage (or tissue death) that can result from prolonged occlusion of arterial blood flow.

The difficulty of suturing a graft to an artery using minimally invasive surgical techniques has effectively prevented the safe use of this technology in both peripheral vascular and cardiovascular surgical procedures. When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulas. When manipulating instruments through cannulas, it is extremely difficult to position tissues in their proper alignment with respect to each other, pass a needle through the tissues, form a knot in the suture material once the tissues are aligned, and prevent the suture material from becoming tangled. Therefore, although there have been isolated reports of vascular anastomoses being formed by minimally invasive surgery, no system has been provided for wide-spread surgical use which would allow such procedures to be performed safely within the prescribed time limits.

As explained above, anastomoses are commonly formed in open surgery by suturing together the tissues to be joined. However, one known system for applying a clip around tissues to be joined in an anastomosis is disclosed in a brochure entitled, "VCS Clip Applier System", published in 1995 by Auto Suture Company, a Division of U.S. Surgical Corporation. A clip is applied by an applying instrument about the tissues in a nonpenetrating manner, i.e., the clip does not penetrate through the tissues, but rather is clamped down around the tissues. As previously explained, it is imperative in forming an anastomosis that tissues to be joined are properly aligned with respect to each other. The disclosed VCS clip applier has no means for positioning tissues. Before the clip can be applied, the tissues must first be grasped and properly positioned with respect to each other, for example by skewering the tissues with a needle as in common suturing techniques and/or with forceps to bring the tissues together. As discussed, it is extremely difficult to perform such positioning techniques in minimally invasive procedures. Therefore, there is currently a need for a system adapted for wide-spread surgical use that is capable of manipulating and positioning tissues in a desired alignment with respect to each other, and thereafter capable of forming an anastomosis in minimally invasive procedures.

SUMMARY OF THE INVENTION

In view of the foregoing, it is an advantage of the invention to provide surgical needles, retainers and surgical fasteners that permit surgeons to perform peripheral vascular and cardiovascular surgery with minimally invasive techniques, without the need to either tie knots or manage a trailing suture.

It is an advantage of the invention to provide surgical needles, retainers and fasteners useful in minimally invasive procedures to replace or bypass a diseased, occluded or injured artery quickly, safely, and reliably.

It is an advantage of the invention to provide surgical needles and retainers that form surgical fasteners useful in constructing an artery-to-graft anastomosis in the abdominal cavity, retroperitoneal space or chest.

It is an advantage of the invention to provide instruments and methods for precisely manipulating these needles and retainers, and for applying the fasteners by minimally invasive surgery.

It is an advantage of the invention to provide fasteners, instruments and methods that permit surgeons to perform minimally invasive surgery by employing many of the same suturing skills and techniques used in open surgery.

It is an advantage of the invention to provide surgical needles, retainers, fasteners and instruments capable of use in constructing other soft tissue anastomoses or joining other soft tissues together by minimally invasive techniques.

It is an advantage of the invention to provide surgical needles, retainers, fasteners and instruments that are also capable of use in traditional open surgery.

These and other advantages are achieved by providing a needle designed to permit surgeons to construct vascular and other anastomoses by minimally invasive surgery, while employing many of the same skills and techniques that are applicable to manipulating conventional suture needles and to constructing such anastomoses with conventional sutures. In accordance with these and other advantages, embodiments of the present invention include a needle and a retainer that when joined together comprise a surgical fastener. The present invention may further include an instrument for applying this fastener for purposes of joining together soft tissues, or creating vascular or other anastomoses in a knotless and sutureless fashion. The needle may also be used for other purposes without the retainer. In a preferred embodiment, the needle is initially held in one jaw of the applying instrument and the retainer is initially held in a retracted position by a second jaw of the instrument. Tissues to be joined, such as a graft and artery, are pierced and manipulated by the needle with the sewing techniques commonly used by surgeons. After the graft and artery have been pierced and brought into close proximity by use of the needle, the surgeon advances the retainer from its retracted position inside the applying instrument, and places the retainer over the needle to form the pinned retainer (a knotless, sutureless surgical fastener). The needles and retainers, together with the instruments and methods to use them, permit an anastomosis between a graft and an artery using minimally invasive techniques.

While the invention is designed primarily for minimally invasive arterial grafting, the invention is also useful for attaching together a variety of other non-vascular soft tissues in the abdominal cavity, retroperitoneal space or chest by minimally invasive techniques. For example, the invention may be used to construct an anastomosis in the stomach, intestine, or colon, or to perform any of the standard anti-reflux operations involving the stomach, esophagus, or diaphragmatic hiatus. The needles, fasteners and instruments of the invention may also be used in an open surgical procedure.

BRIEF DESCRIPTION OF THE DRAWINGS

The above and other advantages of the present invention will be apparent upon consideration of the following detailed description, taken in conjunction with the accompanying drawings, in which like reference characters refer to like parts throughout, and in which:

FIGS. 1A–B show illustrative embodiments of surgical fasteners of the invention (FIG. 1A showing an elevation and plan view of a surgical needle and a retainer; FIG. 1B showing an elevation and plan view of a fastener formed from the needle and retainer of FIG. 1A);

FIGS. 1C–D show additional illustrative embodiments of a surgical needle in accordance with the invention (FIG. 1C showing an elevation and plan view of one needle embodiment; and FIG. 1D showing an elevation and plan view of another needle embodiment;

FIG. 1E is an enlarged view in section through line 1E—1E in FIG. 1D;

FIGS. 9A and 9B are, respectively, plan and elevation views of the retainer holder of the surgical instrument of FIGS. 6A–B;

FIG. 10 is a plan view of the needle holder member assembly of the surgical instrument of FIGS. 6A and 6B; and FIGS. 11A and 11B show, respectively, an illustrative embodiment of a tool for trimming the tips of the needle portion of the surgical fastener of FIGS. 1A–B, and a detailed view of a working end of such a tool.

DETAILED DESCRIPTION OF THE INVENTION

Figure 2A:
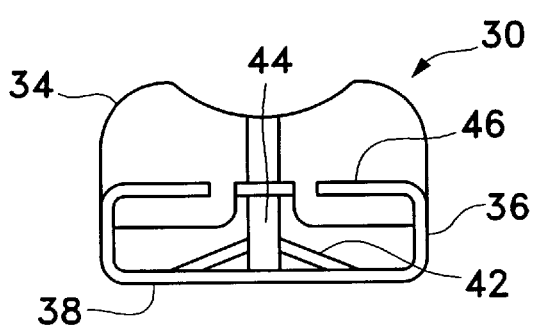
FIGS. 2A–B show views of the retainer shown in FIGS. 1A and 1B (FIG. 2A being an elevation view in section of the retainer and FIG. 2B being a plan view)
Figure 2B:
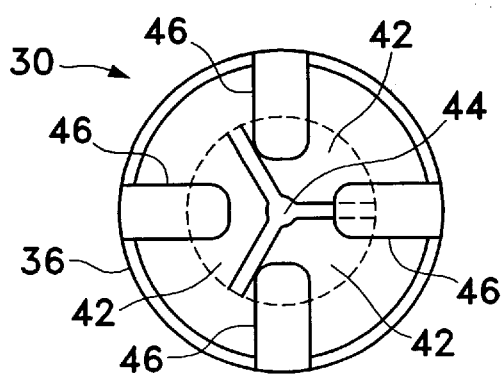

Embodiments of the present invention relate to a pinned retainer surgical fastener for fastening together an artery and a graft, and methods and apparatus for applying the fastener. In a preferred embodiment of the present invention, the fastener may be applied in a minimally invasive surgical procedure, utilizing suturing techniques commonly applied in open surgical procedures. It is also contemplated that the present invention may be used in open surgical procedures. As explained in greater detail below, the pinned retainer surgical fastener according to the present invention may be applied by a hand-held instrument manually or automatedly controlled by a surgeon, or alternatively, the fastener may be applied by a remotely controlled robotic mechanism. Furthermore, although a preferred embodiment of the invention is used to fasten together a vascular artery and a graft, it is understood that the present invention may be used to fasten together tissues, or a tissue and graft, in any surgical procedure where tissues or tissue and graft are to be fastened together. As used herein, the term "tissue" may refer to any vascular passage or other body organ, and the term "graft" may refer to any biological or synthetic graft.

Referring now to FIGS. 1A and 1B, a pinned retainer surgical fastener 32 according to the present invention in general comprises a surgical needle 10, and a retainer 30 capable of being received and fixed on needle 10. The needle 10 and retainer 30 of fastener 32 are capable of securing together tissues such as for example a graft 50 and an artery 52. Needle 10 in general may be used to pierce the graft 50 at a selected location, move the graft to a position near the artery 52, and then pierce the artery at a selected location to precisely and correctly align the graft and artery for connection by a fastener 32. Needle 10 is preferably made of a biocompatible material, and includes a base 12, an elongated shaft 14, and a tip 16. The shaft 14 and tip 16 may be provided with a wide range of shapes, from straight to highly curved, and a variety of different sizes. For example, the shaft and tip may be curved throughout substantially their entire length, as illustrated by shaft 14 and tip 16 in FIG. 1C, or may be curved in only a portion of their length, as illustrated by shaft 14 and tip 16 in FIG. 1D. Needles incorporating such shapes are known in the art. In preferred embodiments of the invention, the needle is preferably provided with substantially the same range of piercing points, curvatures and sizes as commercially available suture needles used with sizes 2–0 to 8–0 sutures. This range of piercing points, shapes, and sizes permits the surgeon to use essentially the same suturing (or sewing) motions that are currently used with conventional suture needles in open surgical procedures, and allows this invention to be used in a wide range of tissue fastening applications. The precise configuration of the needle may vary, depending on for example, the anatomy of the patient, the geometry of the surgical set-up, the area of the body in which the fasteners are to be applied, and the nature, type, and thickness of the tissues that are to be joined together.

The needle must also be strong enough to withstand the forces encountered as the needle is driven through the tissues or graft. The needle is adapted to pierce or otherwise penetrate the structures to be joined. The tip 16 of the needle 10 is shaped into a point designed to penetrate tissues without injuring, tearing, or otherwise affecting the integrity of the tissues. This is largely accomplished by forming the tip 16 with a substantially circular, elliptical, or oblong cross-section, substantially free of a cutting edge. It is understood, however, that needle 10 may have a tip with a cutting edge along its length in alternative embodiments of the invention. Tip 16 of needle 10 may either taper to a point or have a blunt end, depending, for example, on whether the needle is passing through a normal and relatively undiseased artery, a calcified or artrosclerotic artery, or a thinned out, endarterectornized artery. A blunt tip needle may be preferable for use where a surgeon first needs to make a hole in the artery (or other tissues) with a punch. A blunt tip needle could then penetrate through this pre-punched hole. Such a procedure may be preferable in cases involving a severely calcified artery.

The shaft 14 may be joined to, or formed integrally with, the base 12 of the needle 10 at a central portion of the base as shown in FIGS. 1A and 1B. The shaft may alternatively be offset from the center of the base, and joined to the base close to the edge of the base as shown in FIGS. 1C and 1D. The needle 10 may also include markings spaced at selected intervals along a portion or the entire length of the shaft 14, as shown in FIG. 1C. This provides the surgeon with a visual indication of the position on the shaft of the tissues being joined relative to the base. The markings also allow the surgeon to visually judge the position of the retainer during application to assist the surgeon in placing the retainer so that it is secured onto the shaft without overcompressing and potentially damaging the tissues being joined. In a preferred embodiment, the shaft is provided with a constant cross-sectional diameter and shape along at least a portion of its length (referred to as the retainer-engaging portion of the shaft). In this way, the surgeon is able to apply the retainer at any point along the retainer-engaging portion of the shaft and achieve substantially the same degree of secure engagement. This allows the surgeon to select the most suitable position for the retainer along the shaft, depending on the nature and thickness of the tissues to be fastened.

In embodiments of the invention, the retainer-engaging portion of the shaft may be provided with ridges, or a grained surface, to ensure a secure engagement of the shaft and retainer once the retainer is located thereon. Alternatively, the retainer-engaging portion of the shaft may include a detent located at a predetermined location on the retainer-engaging portion of the shaft. In this embodiment, a retainer may be provided that moves relatively freely along the shaft until a corresponding needle-engaging portion of the retainer snaps into, or otherwise engages within the detent, whereupon the retainer is fixed on the shaft. The location of the detent may vary, depending on the type and thickness of the tissues to be joined. Preferably, the detent is provided at a position where the tissues are held firmly together once the retainer engages within the detent.

The base 12 of the needle 10 is configured to be releasably held by the distal end of a fastener applying instrument, discussed hereinafter. This configuration allows the surgeon to control the needle during its penetration through the graft, artery or other tissues, and to release and detach the needle from the instrument once the retainer has been applied and the fastener is complete. The base may have at least one slot or flange to permit the needle to be temporarily but securely locked in the distal end of the applying instrument of the invention. For example, as shown in FIGS. 1A and 1B, base 12 may include a groove 24, or similar configuration, which may be gripped by an engaging mechanism on the applying instrument (described hereinafter). Alternatively, base 12 may include tangential slots, or similar configuration, such as shown in FIGS. 1C and 1D which may similarly be gripped by an engaging mechanism on the applying instrument. These slots or flanges may also assist in preventing the needle from rotating or moving during use, so that the needle has a constant orientation with the needle holder member of the applying instrument. As shown in FIGS. 1A and 1B, the base may also have additional flanges 26 on the base adopted to engage portions on the applying instrument to assist in preventing the needle from rotating or changing orientation during application. For example, flange portions 26 of the needle of FIGS. 1A and 1B may engage flat edge 156 of the needle support member 102 shown in FIG. 10 and discussed hereinafter. As would be appreciated by those skilled in the art, base 12 may be formed of various configurations to facilitate releasable gripping and a fixed orientation of the needle on the fastener applying instrument.

The base 12 and the retainer 30 each have opposing substantially planar surfaces that cooperate to secure together the tissues to be joined. The graft and artery are held together on the shaft by the retainer on one side and by the base on the other side, as shown in FIG. 1B. Although the graft 50 is shown skewered first and in contact with the base 12 in FIG. 1B, it is understood that the artery 52 may alternatively be skewered first, and then the graft skewered second.

Referring to FIGS. 1A–D, base 12 includes a substantially planar upper surface extending substantially perpendicular to an adjacent portion of shaft 14. As described in greater detail below, an applied retainer has a corresponding surface that contacts either the artery or the graft on the other side of the anastomosis. These corresponding surfaces of the base and retainer are large enough so that a force applied to the graft and artery by the applied fastener effectively secures the artery and graft together, preferably achieving a substantially hemostatic seal. When using the retainer to join an artery and a graft, the needle creates a hole in the artery as it is driven through the vessel. Even if that hole is substantially larger than the shaft of the needle itself, sufficient force is exerted by the needle base and retainer on the arterial wall and the graft to prevent any significant leakage of blood from the artery through the hole. This applied force must not be so large that it interferes with the natural, biological processes that support the health of the tissues, including the movement of fluids, nutrients, oxygen, etc. within those tissues. These surfaces must also be large enough to prevent the fastener from migrating acutely or chronically through the graft or the artery. After the retainer is applied onto the shaft, the separation or distance between the opposing surfaces of the retainer and the base remains substantially constant and parallel to each other. However, it is not necessary that the opposing surfaces of the base and retainer be parallel, provided that these surfaces provide an appropriate amount and distribution of force to securely fasten the tissues together without injuring the tissues.

The base may have a variety of shapes and sizes, with the upper surface of the base having substantially the same shape as the corresponding surface of the retainer. This shape is preferably circular, elliptical, or oblong. Preferably, the upper surface of the base (whether substantially circular, elliptical or oblong) has a minimum distance measured from one edge to the opposite edge across its narrowest dimension between about 0.3 to 0.25 inches. Preferably, the upper surface of the base has a surface to contact structures to be joined with an area between about 0.01 and 0.2 square inches. The particular size and shape of this surface may be chosen depending on the nature, thickness, and location of the tissues that are being approximated.

As stated, a preferred embodiment of the invention is used to fasten together a vascular artery and a graft. However, the needle and retainer of the invention may be used in substantially the same fashion to attach a variety of nonvascular soft tissues together, whether in the chest, abdominal cavity, or retroperitoneal space (for example, the stomach, the intestine, the diaphragmatic hiatus, etc.). In each case, the soft tissues to be joined together are skewered onto the shaft of the needle, and sandwiched between the base of the needle and the retainer.

The needle is constructed of any biocompatible material having sufficient hardness and strength for insertion through a graft, an artery (even if calcified), or other soft tissues in the chest, abdominal cavity, or retroperitoneum. The needle also has sufficient hardness and strength to withstand the force of application of the retainer. Preferably, the needle is made of non-absorbable, biocompatible metals, such as stainless steel, tungsten, or titanium. It may also be made of non-absorbable plastics, such as Teflon or nylon, or biodegradable polymers, such as polyglycolic acid. For artery-to-graft anastomoses, a non-absorbable fastener is needed. However, absorbable fasteners may be used if appropriate to the clinical situation (such as in joining certain soft tissues together temporarily or constructing anastomoses in the stomach, intestine, or colon). If the clinical application requires an absorbable fastener (for example, in creating an intestinal anastomosis), then the needle may be made of a bioabsorbable material.

Details relating to the retainer 30 will now be described with reference to FIGS. 1A–1B and 2A–4B. The retainer 30 is preferably comprised of two members: a base 36 (FIG. 2A) of resilient, hard material, and an elastomeric cap 34 affixed to the base. The cap 34 may be secured to the base 36 in any suitable but permanent fashion. The base 36 is comprised of a thin plate 38 of uniform thickness, and two or more tangs 42 formed in the plate, which tangs define an aperture 44. The aperture 44 is precisely sized and configured to receive and securely engage the shaft of the needle. In a preferred embodiment, the aperture 44 may have a diameter slightly less than that of the shaft 14 to ensure a snug fit of the retainer over the needle. The retainer is constructed to slide easily onto the shaft with minimal force, but to strongly resist forces tending to move the retainer in the opposite direction. This is primarily accomplished by the tangs 42 which protrude diagonally upward out of the plate 38 and lie in engagement with the shaft 14 once the retainer is positioned over needle 10.

As the retainer is pushed onto the shaft toward the base of the needle, the thin plate and/or the tangs are deformed. This deformation reduces the force required to apply the retainer onto the needle. Because the plate is made of a resilient, elastic material, the plate and tangs create a spring-like contact force with the retainer that assists in securing the retainer and needle together. The opposite occurs if force is applied to attempt to move the retainer away from the base of the needle. If forces are created that attempt to move the retainer away from the base, the deformed plate strongly resists deformation in the opposite direction, and strongly resists movement away from the base. This permits the forces needed to apply the retainer to be significantly lower than the forces that would be required to remove the retainer.

The deformation of the plate converts forces tending to move the retainer away from the base into gripping forces applied by the tangs against the shaft of the needle. Additionally, the tangs are formed with sharp edges. As the retainer is applied, the deformation of the plate causes portions of the sharp edges of the tangs to contact the surface of the shaft. If forces are applied tending to move the applied retainer away from the base of the needle, those forces will cause the edges of the tangs to dig into the shaft, and further assist in preventing any significant movement of the retainer relative to the shaft.

Figure 4A:
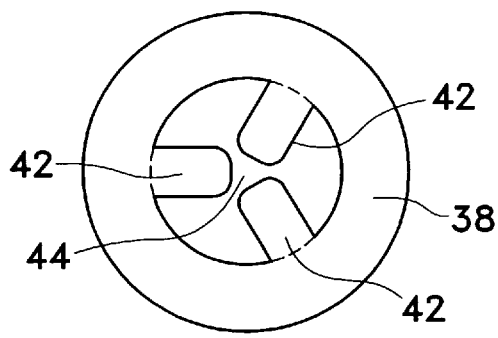
FIGS. 4A–B are plan views of alternative illustrative embodiments of tangs of the retainer shown in FIGS. 2A–B.
Figure 4B:
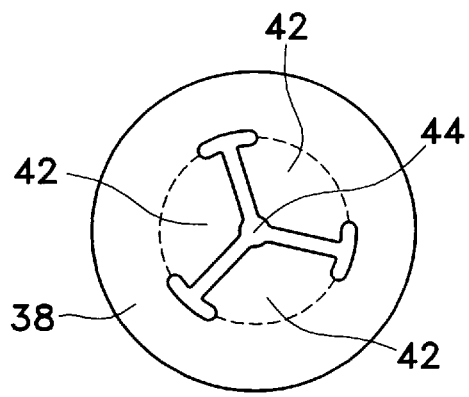

Many plate and tang geometries are capable of use to securely engage the retainer and needle in these ways. Preferably, the tangs are formed, cut or slit in a symmetrical pattern, and formed or bent out of the plane of the plate 38 as shown, for example, by tangs 42 in FIG. 2A. Preferably, there are three separate tangs 42 defining the central aperture of the retainer, so that at least three points of contact are established with complementary surfaces on the shaft of the needle. Plate 38 and tangs 42 may have varied shapes and sizes. Two alternate forms of plate 38 and tangs 42 are shown in FIGS. 4A and 4B. Alterations of the particular shape and size of the plate and tangs may be employed to adjust the forces needed to insert and remove the retainer. The shape and size of the plate and tangs must be consistent with the need for this surface of the retainer to provide an appropriate distribution of force on tissues held between base 12 and retainer 30. The choice of the particular shape and size for tangs 42 is a function of the surgical procedure to be performed and characteristics of the tissues to be joined. Preferably, the tangs of the retainer have greater hardness than the shaft. This difference in hardness assists the tangs in gripping the shaft by digging into and slightly deforming the surface of the shaft. When made of metal, the retainer is preferably made of the same metal type material as the needle to prevent electrolysis and galvanic reactions between the needle and the retainer.

Figure 4C:
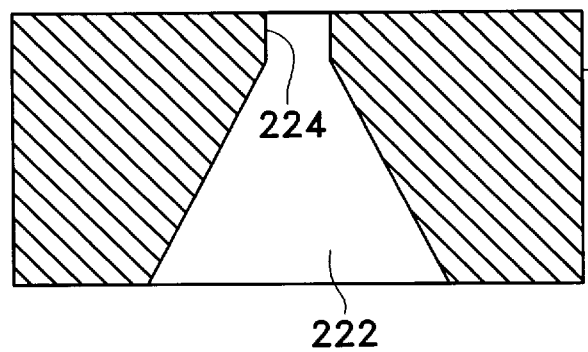
FIG. 4C is a cross-sectional side view of a retainer according to an alternative embodiment of the invention.

An alternative embodiment of the invention shown in FIG. 4C may comprise a retainer 220 having a funnel shaped aperture 222 formed therein. Thus, when the retainer is brought down over the needle, a center of the aperture 222 need not initially exactly align with the tip of the needle. Rather, a slight initial misalignment may exist, and the retainer will still be correctly positioned over the needle. The retainer 220 of FIG. 4C is preferably formed of plastic, or similar rigid material, and preferably of a softer material than the needle received through aperture 222. An upper portion 224 of the aperture 222 should have a diameter approximating that of the retainer-engaging portion of the shaft 14. Thus, a tight fit of the retainer on the shaft is ensured, and relative movement of the retainer and shaft is substantially prevented once the retainer is located thereon. In a preferred embodiment, the retainer 220 is used with a ridged or grained shaft as previously described. It is understood that the retainer 30 shown in FIG. 2A may also have a funnel shaped aperture to provide for an initial misalignment of the needle and retainer aperture. In such an embodiment, the plate 38 may be provided with a thickness, such that a lower surface of the plate (the surface juxtaposed to the base 12) may have a relatively large aperture which tapers inward toward the upper surface of the plate to thereby form a funneled aperture in the plate 38. As would be appreciated by those skilled in the art, the retainer may be provided with other funnel configurations to allow correct positioning of the retainer on the needle despite an initial misalignment of the needle with a center of the retainer aperture.

The cap 34 of retainer 30 is attached to the retainer base 36, and is configured to substantially surround or shield the shaft 14 after application of the retainer. The base 36 may include tabs 46 projecting inwardly from a skirt portion of base 36. Cap 34 may then be molded onto base 36 and plate 38 such that it encapsulates tabs 46, thereby coupling cap 34 to base 36. The cap substantially prevents the end of the shaft of an applied fastener from protruding above the retainer, where it might otherwise injure adjacent tissues or structures. Cap 34 also provides stability to an applied retainer by limiting rocking or pivoting motions around the point at which the retainer plate contacts the shaft. Preferably, the cap is made of a soft elastomeric material, such as polytetrafluoroethylene. This material allows the cap to be depressed prior to trimming off the tip of the needle. When the cap then elastically returns to its original shape, the cap extends beyond, and more effectively shields tissues and structures from, the end of the needle. Cap 34 may also include a hole substantially axially aligned with aperture 44 to enable shaft 14 of needle 10 to pass more easily therethrough.

As discussed above in connection with FIG. 1C, base 12 of needle 10 may have a non-circular surface to contact structures to be joined, and shaft 14 may be offset from the geometric center of the base. Preferably, the design of retainer 30 is matched to the design of the base of the needle. For example, retainer 30 may have an oblong or elliptical shape as shown in FIG. 3, for use with a corresponding oblong or elliptical shape of needle base 12 of FIGS. 1A–B. The plate 38 preferably has a surface corresponding to that of the base 12, with a distance measured from one edge to the opposite edge across its narrowest dimension between about 0.3 and 0.25 inches. Preferably, the plate 38 also has a surface to contact structures to be joined with an area between about 0.01 and 0.25 square inches. Additionally, as with needle 10, the retainer 30 is preferably formed of a non-absorbable, biocompatible material. However the retainer 30 may be formed of bioabsorbable materials in alternative embodiments of the invention. Aperture 44 may be somewhat offset from the geometric center of retainer 30 in FIGS. 2A–B and 3 for use with the offset needles of FIGS. 1C and 1D.

After the retainer is located in proper position over the needle, the tip 16 is preferably removed. The tip may be manufactured as an integral part of the needle. In this case, the tip needs to be cut off and removed after the retainer has been applied. For example, shaft 14 and tip 16 may comprise an integral unit as shown in FIGS. 1A–1C. Alternatively, the tip can be manufactured as a separate piece and then "swedged on" or otherwise releasably attached to the shaft. Such an example is shown in FIG. 1D, in which shaft 14 includes cup 18 and tip 16 includes a pin 20. The pin 20 is fits within the cup 18 and is frictionally held therein to removably attach the tip 16 to the shaft 14. In this form, after the retainer has been applied and is in position, the tip may be separated from the shaft at the point of attachment. It is understood that the positions of the cup 18 and pin 20 may be reversed relative to the shaft and tip in an alternative embodiment of the invention. It is further understood that the mechanism for removably attaching tip 16 to shaft 14 in the two-part needle may be formed of varying configurations, with the provision that the size of the joint between the tip and shaft not be substantially larger than portions of the needle adjacent to the joint.

Figure 5:
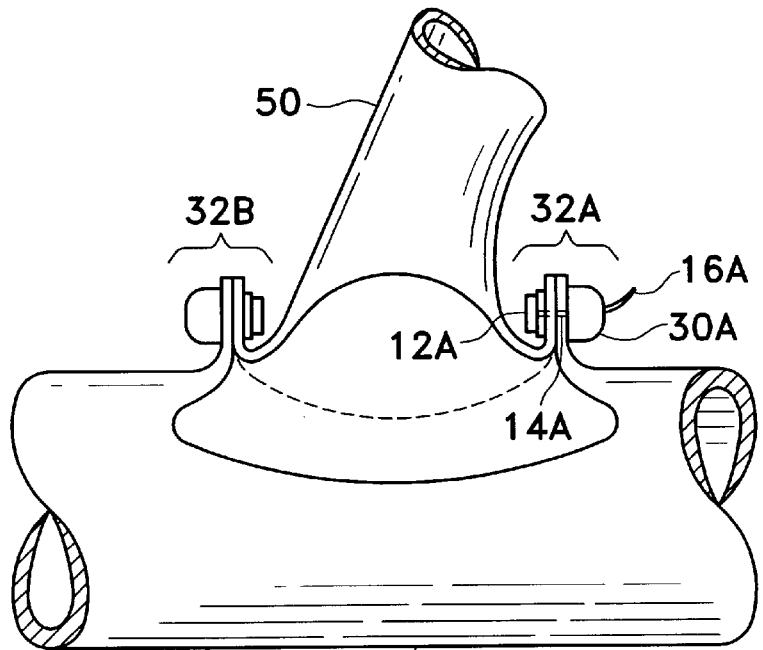
FIG. 5A is a schematic drawing, not to scale, illustrating the use of the fastener of FIGS. 1A–B to form a graft-to-artery anastomosis in accordance with the invention.
FIGS. 5B–5D are perspective and side views of an alternative embodiment of the pinned retainer for forming a graft-to-artery anastomosis in accordance with the invention.

FIG. 5A shows an illustrative use of surgical fasteners 32*a* and 32*b* in accordance with the principles of the present invention. Graft 50 is joined to artery 52 using fasteners 32*a* and 32b. Referring to fastener 32a as an example, the needle of fastener 32a is first used to pierce graft 50 and artery 52 near the site of the anastomosis. Retainer 30a is then pressed onto shaft 14a, thereby sandwiching portions of graft 50 and artery 52 between retainer 30a and needle base 12a. Subsequently, tip 16a is removed so that surrounding tissues will not be injured. Fastener 32b, which may be applied in the same manner as fastener 32a, illustrates a completed fastener with the tip removed. A series of such fasteners are applied around the circumference of the graft to form the anastomosis. Although a preferred embodiment of the invention utilizes both the needle 10 and retainer 30, it is understood that an alternative embodiment of the invention may comprise just the needle 10 gripped by the applying instrument described below. In this alternative embodiment, the needle may be manipulated by controls in the applying instrument to skewer and precisely align tissues, or tissue and graft, which may thereafter be fastened together by conventional methods.

Figure 5B:
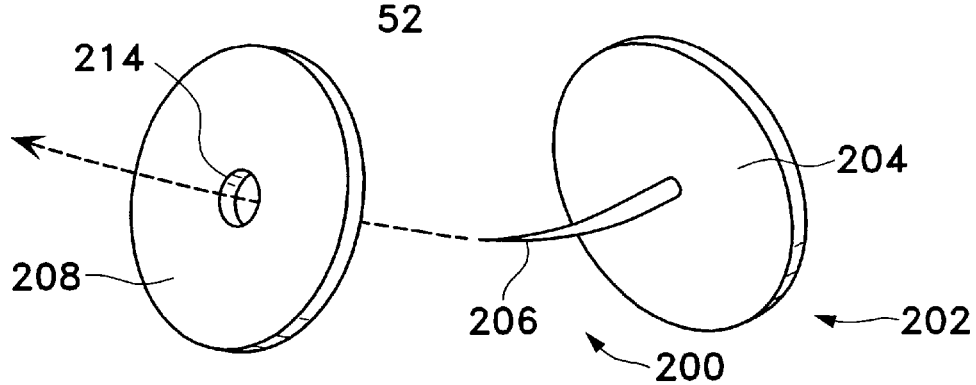
Figure 5C:
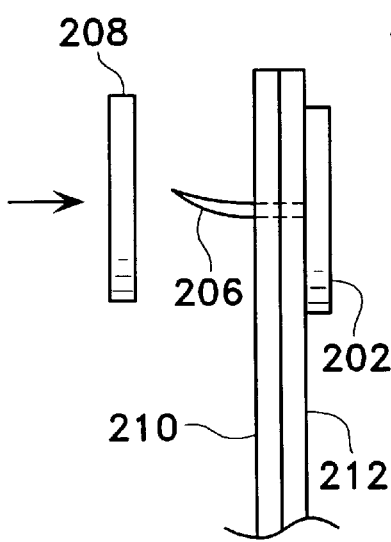
Figure 5D:
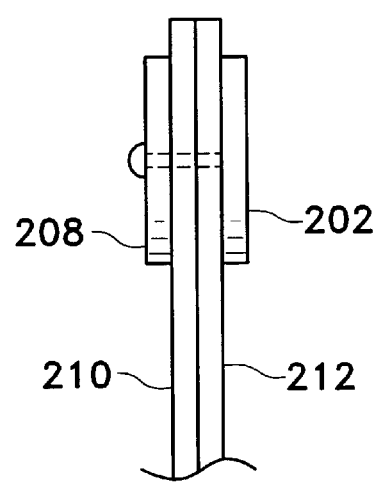

FIGS. 5B–5D illustrate an alternative embodiment of a pinned retainer fastener according to the present invention. The fastener 200 according to this embodiment comprises a needle 202 having a base 204 and a shaft 206, and a retainer in the form of a washer 208. In general, the tissues are skewered by the needle 202 as described above, and then the washer 208 is placed over the shaft 206 so that the washer is juxtaposed to the base 204 with tissues 210 and 212 positioned therebetween. Once the washer is properly positioned with respect to the base so that the tissues are sandwiched between the washer and base with a desired pressure exerted over the area of contact with tissues 210, 212, the shaft of the needle is bent, flanged, crimped or otherwise deformed to fix the washer 208 in position, as shown in FIG. 5D.

Needle 202 shown in FIGS. 5B–5D may be formed of the same materials and sizes as needle 10 of FIG. 1A, and may be formed of various configurations facilitating deformation of the needle shaft once the washer 208 is properly positioned. For example, the needle may have a tip integrally formed thereon, which tip is either bent or crimped down over the washer 208 once the washer is positioned. Alternatively, the needle may be a two-part needle as described above, such that the tip is removed after the washer 208 is in position. In such an embodiment, after the washer is positioned and the tip is removed, the portions of the needle shaft 206 protruding through the washer may be bent or crimped. Alternatively, needle 202 may have a hollow interior such that, after the washer is positioned and the tip is removed, the edges of the shaft may be bent outward, or flanged, to thereby secure the washer in position juxtaposed to the base 204. Those skilled in the art would appreciate that needle 202 may be formed of other configurations and/or deformed by other methods to secure the washer 208 in place once the washer is properly positioned.

Figure 3:
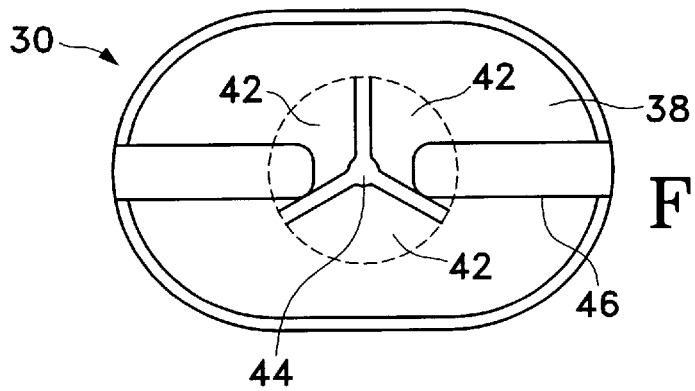
FIG. 3 shows a plan view of an alternative illustrative embodiment of a retainer of the invention.

Washer 208 may be made of the same materials and sizes as retainer plate 38 shown in FIG. 2A. In a preferred embodiment, the washer 208 may be single planar member, with a hole 214 through which the needle shaft 206 passes. The size of hole 214 is preferably slightly greater that the diameter of shaft 206. In an alternative embodiment, the washer may be formed of two layers. A first layer in contact with the tissues 210 or 212 may be rigid, as in plate 38 of FIG. 2A, and a second layer adhered to the first layer may be formed of an elastomeric material, such as cap 34 of FIG. 2A. In this embodiment, the needle may be bent down or otherwise deformed into the elastomeric material, to prevent any surrounding tissues from contacting the deformed end of the needle. It is understood that other features of the needle 10 and retainer 30 described with reference to FIGS. 1A–5A may be incorporated into the needle 202 and washer 208 shown in FIGS. 5B–5D in further embodiments.

Figure 6A:
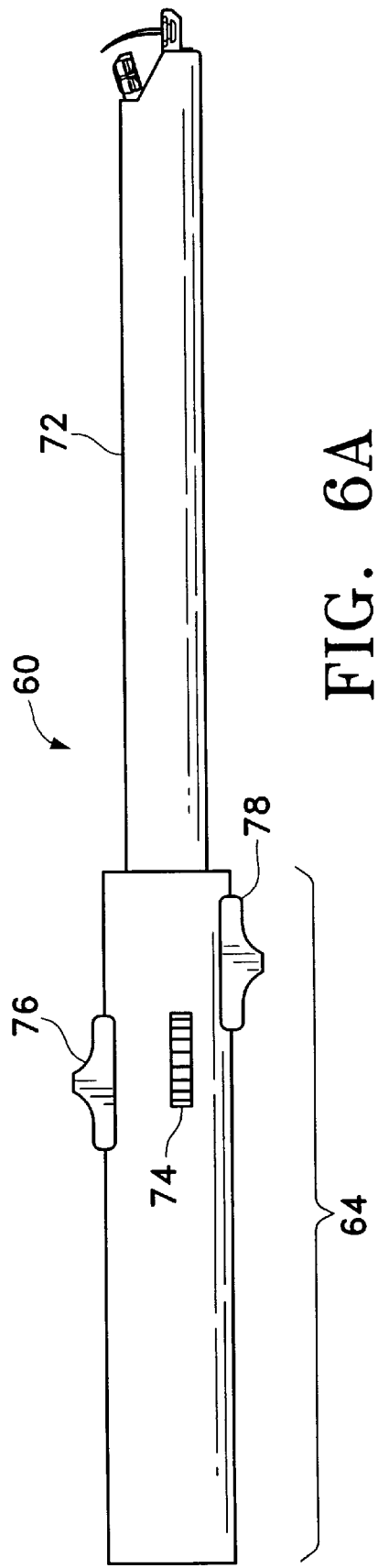
FIGS. 6A and 6B are, respectively, elevation and plan views of an exemplary surgical instrument for applying the surgical fastener of FIGS. 1A–B.
Figure 6B:
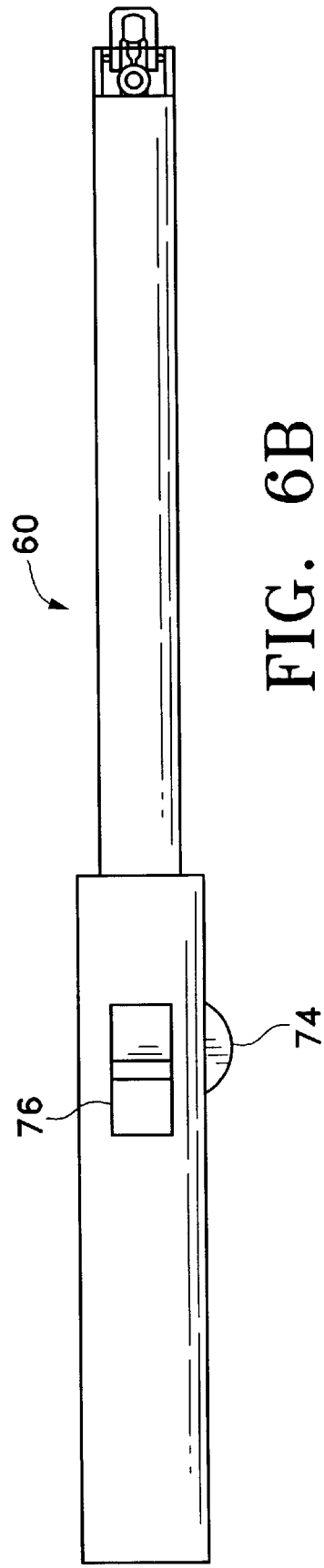

In addition to the pinned retainer described above, embodiments of the present invention also include an instrument for applying the pinned retainer in either minimally invasive or open surgical procedures. Referring now to FIGS. 6A and 6B, the pinned retainer applying instrument 60 is shown having a distal or working end 62, a proximal or handle end 64, and a shaft 72 between the proximal and distal ends. As explained hereinafter with respect to FIGS. 7–10, working end 62 includes a needle holder member 102, a retainer holder member 112, and a clip 140, which components cooperate together to apply the pinned retainer fastener 32. As further explained hereinafter with respect to FIGS. 6A–10, the handle end 64 includes control mechanisms for controlling the operation of the needle holder member 102, the retainer holder member 112, and the clip 140.

Shaft 72 may be either straight or curved, and is preferably made of a suitable rigid material, such as stainless steel, reinforced plastics, or composite materials, so that a surgeon may precisely control the working end of the instrument during surgery. Preferably, shaft 72 is about 5–10 millimeters in diameter so that it fits through and may be used with conventional canulas, but it may be as large as about 20 millimeters in diameter. Shaft 72 may have a variety of lengths suitable to particular surgical situations, and is preferably about 15–27 centimeters long. The shaft houses drive rods which couple the various controls on handle end 64 with the above-named components in working end 62, thus permitting the pinned retainer fastener to be manipulated and formed. The particular size, diameter, length, and configuration of the instrument may vary depending on the size and shape of the needle, the geometry of the tissues to be joined, or the artery to be grafted, anatomic variations, and the size of the surgical space and structures on which the surgeon is operating.

Figure 8A:
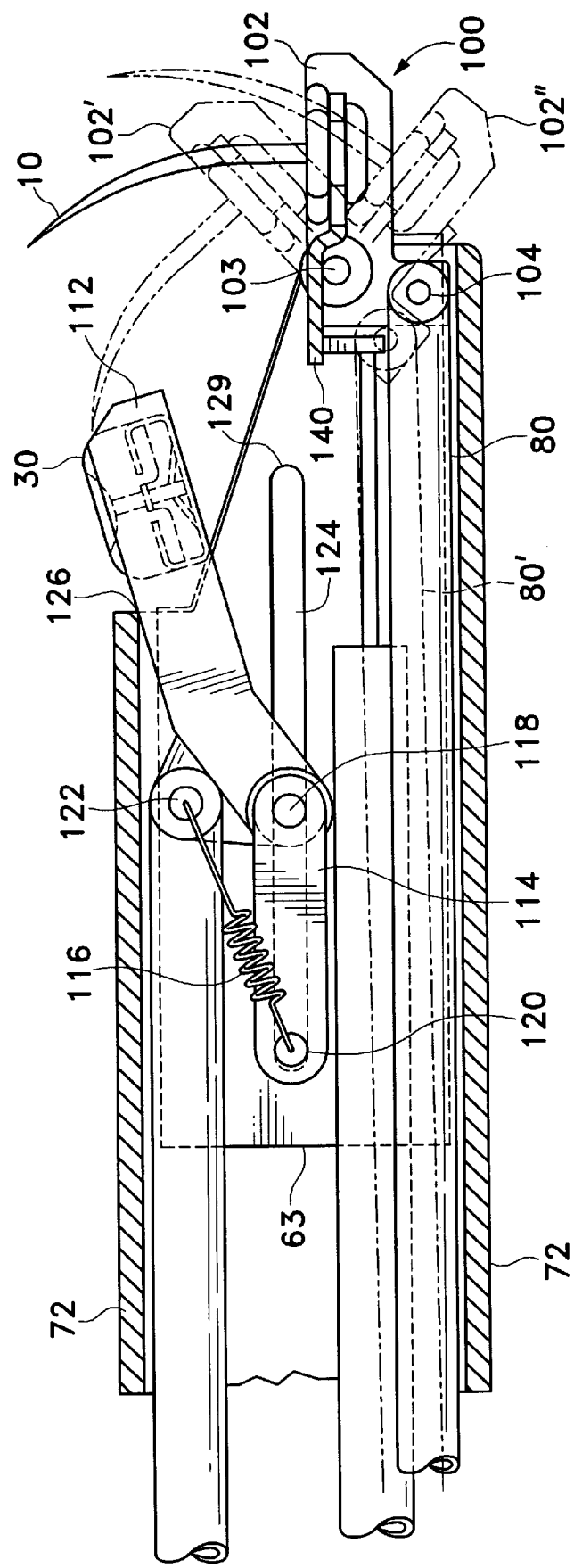
FIGS. 8A and 8B are elevations, partially in section, of the working or distal end of the exemplary surgical instrument of FIGS. 6A–B (FIG. 8A shows some of the positions in which the needle may be oriented relative to the instrument while applying the surgical fastener of the present invention and FIG. 8B shows some of the positions in which the retainer is held during application)
Figure 8B:
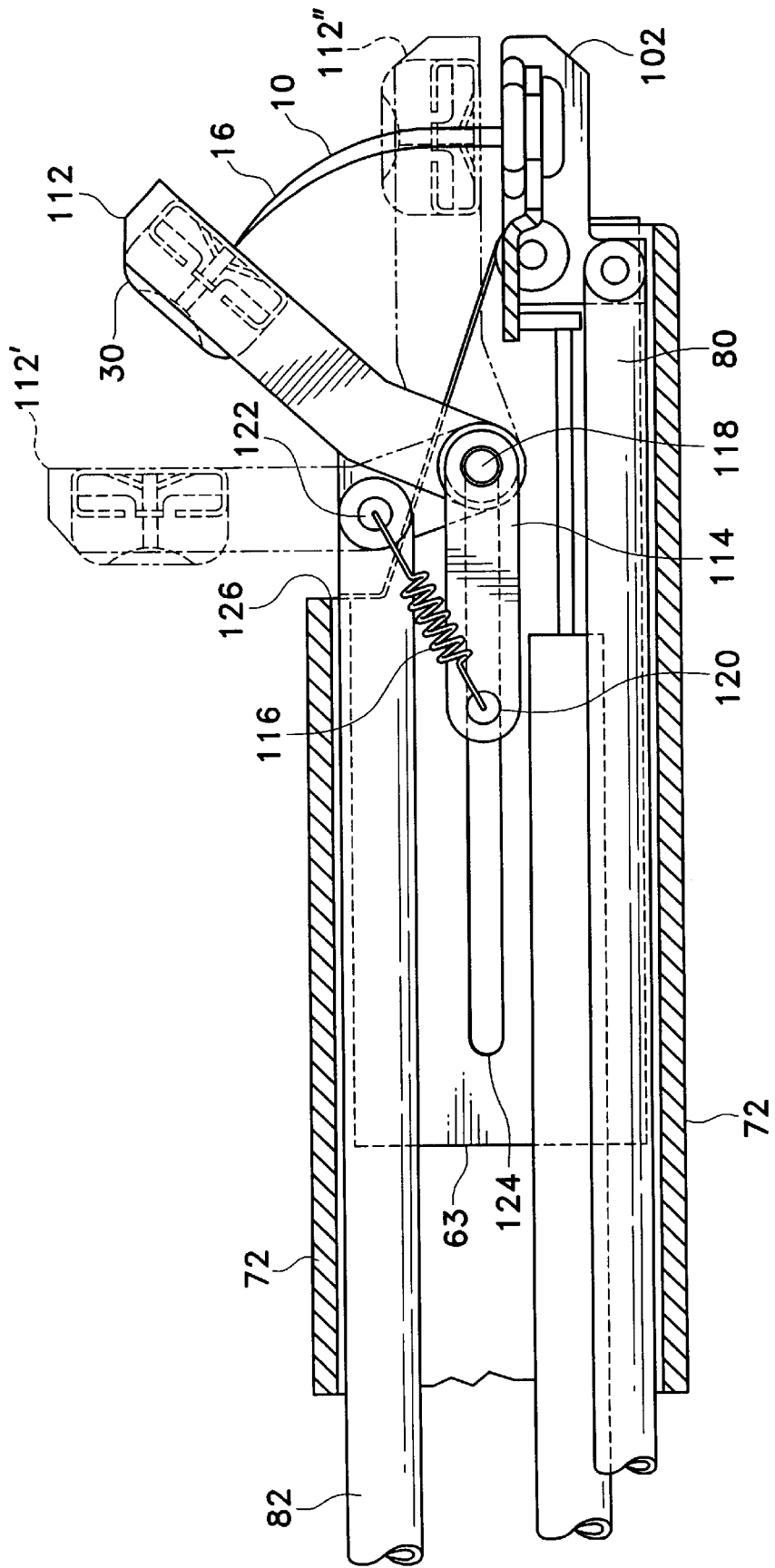

Referring now to FIGS. 8A and 8B, distal end 62 includes a needle holder assembly 100 having a needle holder member 102. Needle holder member 102 is provided for firmly but releasably gripping base 12 of needle 10, and for pivoting needle 10 with one degree of freedom relative to shaft 72 (as indicated by the positions of the needle holder member at 102, 102', and 102"). In a preferred embodiment, the needle holder member may articulate through at least about 90°. However, specific surgical procedures may employ either larger or smaller ranges of motion. The elongated shaft of the instrument allows the surgeon to rotate the instrument about the longitudinal axis of the instrument. These features provide the surgeon with a wide range of freedom to orient the needle relative to the tissues to be skewered and joined together.

In operation, prior to insertion of the instrument to the surgical site, base 12 of needle 10 is inserted into a hole, or recess, 155 (FIG. 10) in needle holder member 102. Hole 155 has a shape corresponding to the base 12 of needle 10. Flat edges 156 are provided to engage flange 26 (FIGS. 1A and 1B) to prevent rotation of the needle 10 in hole 155. As explained hereinafter, the needle is held in place by clip 140.

Figure 7:
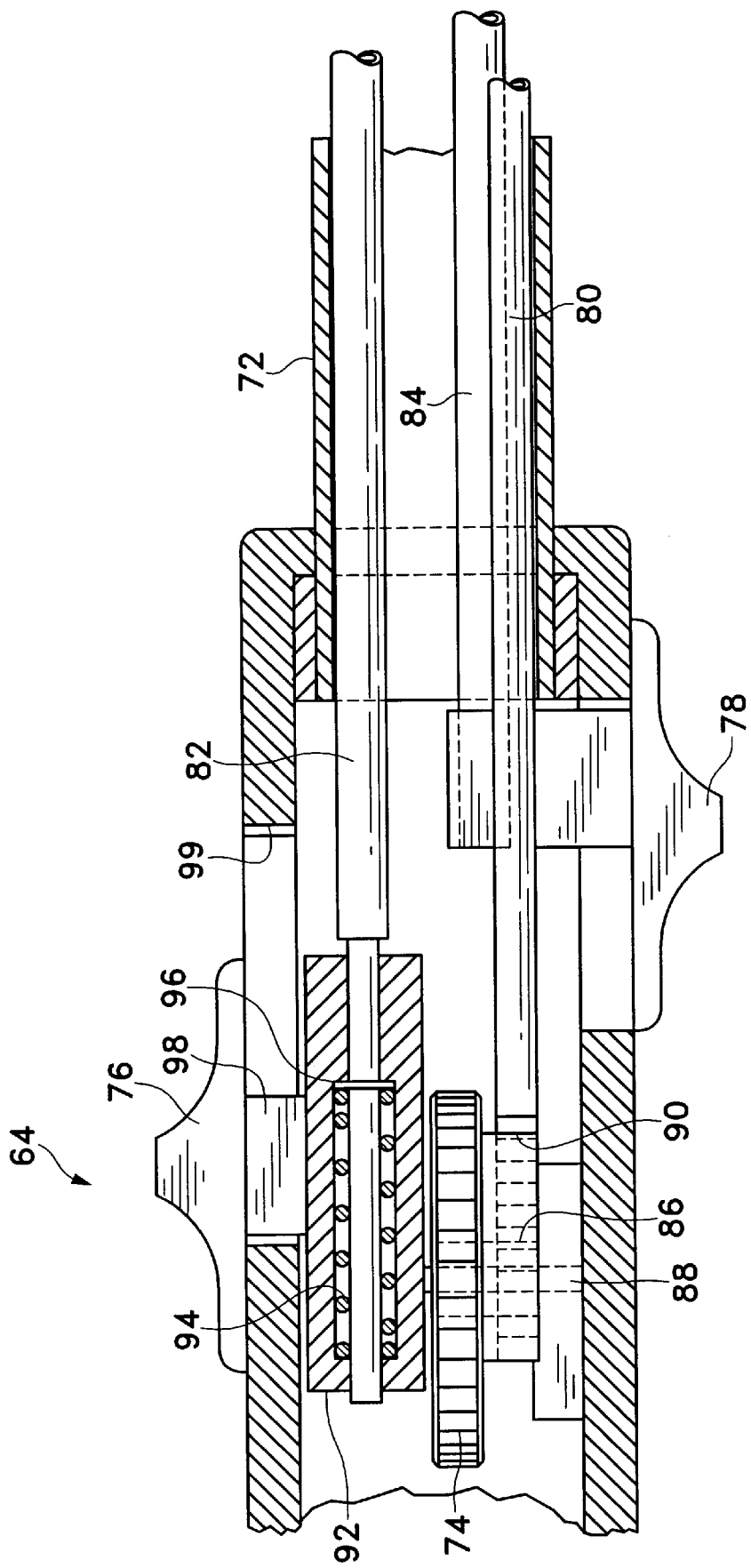
FIG. 7 is an elevation view, partially in section, of an illustrative embodiment of the handle of the instrument of FIGS. 6A and 6B.

Needle holder member 102 may be articulated as follows. As shown in FIG. 7, handle end 64 includes a thumbwheel 74 for controlled manual rotation by a surgeon. Thumbwheel 74 is mounted on axle 88 with pinion 86 so that rotation of thumbwheel 74 causes an equivalent rotation of pinion 86.

A rack gear 90 is coupled to drive rod 80, and is juxtaposed between various guides (not shown) so that teeth on rack gear 90 matingly engage with teeth on pinion 86. This rack and pinion assembly converts rotational movement of thumbwheel 74 into longitudinal motion of drive rod 80. Referring again to FIGS. 8A and 8B, drive rod 80 is pivotally mounted to needle holder member 102 by a pin 104. Needle holder member 102 is in turn pivotally mounted on an axle 103, thus allowing needle holder member 102 to pivot with respect to shaft 72 about axle 103. As would be appreciated by those skilled in the art, rotation of thumbwheel 74 resulting in a proximal (i.e., rightward with respect to the view shown in FIGS. 7, 8A and 8B) motion of drive rod 80 will cause a corresponding counterclockwise rotation of needle holder member 102 and needle 10 about axle 103 with respect to the view shown in FIG. 8A. Such movement of thumbwheel 74 may be used to move the needle holder member 102, and consequently needle 10, for example to a position 102" shown in phantom on FIG. 8A. Conversely, rotation of thumbwheel 74 which results in a distal (i.e., leftward with respect to the view shown in FIGS. 7 and 8A) motion of drive rod 80 will cause a corresponding clockwise rotation of needle holder member 102 and needle 10 about axle 103 with respect to the view shown in FIG. 8A. Such rotation of thumbwheel 74 may for example be used to rotate needle holder member 102, and consequently needle 10, from its home position as shown in FIG. 8A to its position at 102' shown in phantom.

When a surgeon is inserting instrument 60 into a patient, thumbwheel 74 is manipulated to pivot needle holder member 102, and consequently needle 10, to a closed position shown at 102' in FIG. 8A, so that needle 10 will not interfere with passing working end 62 through a canula to the surgical site. After insertion, a surgeon may manipulate thumbwheel 74 to pivot needle holder member 102 and needle 10 as required. For example, a surgeon may pivot needle holder member 102 to a fully open position 102" to skewer a graft, and then return the needle holder member to a home position 102 or a closed position 102' to prevent the graft from falling off while the graft is positioned adjacent to an artery. Subsequently, thumbwheel 74 may again by manipulated to position needle holder member 102 at open position 102" so that needle 10 can skewer the artery to be joined with the graft. In some cases, a surgeon may wish to fix the position of needle 10 with respect to working end 62. Various known mechanisms (not shown) such as thumbwheel detents or adjustable drag devices, as well as drive rod clamps and the like may be provided for this purpose.

While piercing and manipulating grafts, arteries, or other tissues, various forces are applied to needle 10. These forces are passed through needle 10 to needle holder assembly 100. Therefore, needle holder assembly 100 must be sufficiently strong to withstand these forces, and needle holder member 102 must be capable of maintaining the needle 10 in a fixed position as selected by the surgeon. In a preferred embodiment of instrument 60, loading forces applied to needle 10 are transmitted through drive rod 80 and thumbwheel 74, so that a surgeon receives tactile feedback from instrument 60 as the surgery is progressing.

As shown in FIGS. 8A and 8B, working end 62 further includes retainer holder member 112. In general, retainer holder member 112 is provided to support a retainer 30 while tissues are being skewered by the needle 10, and to subsequently position the retainer 30 over the needle 10. The retainer holder member 112 is connected to drive rod 82, which is in turn connected to a slide 76 in handle end 64, as shown in FIG. 7. In positioning a retainer on the needle, it may be desirable to limit the force with which the retainer is applied so as to prevent the fastener from applying too much pressure on the fastened tissues. Additionally, during use of the instrument 60, it may be possible that the retainer holder member becomes bound, or otherwise prevented from moving, as for example if a retainer and a needle are not correctly aligned with each other upon an attempt to locate the retainer on the needle. Therefore, in a preferred embodiment, a force limiter may be provided between the slide 76 and the drive rod 82 to limit the force exerted on drive rod 82 and retainer holder member 112.

The force limiter is comprised of a housing 92, a spring 94 and a pin, or washer, 96. Slide 76 is fixedly mounted with respect to housing 92 such that translation of slide 76 within slot 99 will cause a one-to-one translation of housing 92. Spring 94 is mounted within housing 92, with a first end abutting against the rear of the housing 92 and a second end abutting against washer 96. The washer 96 is fixedly mounted on drive rod 82. With this configuration, a distal movement (i.e., to the right in FIG. 7) of the slide 76 and housing 92 will either: 1) move the spring 94 and drive rod distally (where there are no substantial forces opposing movement of drive rod 82); or 2) compress the spring 94 between the rear of the housing 92 and the washer 96 (where the pressure exerted by the retainer on the tissues has reach a predetermined limit, or the drive rod is otherwise prevented from moving). In this way, slide 76 may be actuated to move drive rod 82 distally where the drive rod 82 is free to move, but, where there are excessive forces on the drive rod resisting movement, a distal movement of slide 76 will not forcibly move rod 82, which forced movement could otherwise damage the tissues, rod 82, retainer holder member 112 and/or needle 10. It is understood that force limiters of other known configurations may be used in alternative embodiments of the invention. Moreover, it is understood that slide 76 may be coupled directly to the drive rod 82 in alternative embodiments of the invention.

Referring to FIGS. 8A and 8B, retainer holder member 112 is pivotally attached to drive rod 82 at a pin 122, and retainer holder member 112 is also pivotally attached to a first point on a carriage 114 by a pin 118. Retainer holder member 112 is additionally coupled to a second point on carriage 114 via a spring 116 attached between pin 122 and a pin 120. Spring 116 biases carriage 114 distally with respect to the retainer holder member 112. Additionally, as retainer holder member 112 is mounted to plate 114 at pin 118, spring 116 biases retainer holder member 112 to rotate counterclockwise about pin 122. Working end 62 further includes a support member 63 having a slot 124 formed therein. Pins 118 and 120 of carriage 114 are mounted and ride within slot 124 such that carriage 114 is free to translate distally until pin 118 abuts against an end 129 of slot 124.

In FIG. 8A, retainer holder member 112 and carriage 114 are shown in their retracted position. It is a feature of the present invention that while inserting working end 62 to the surgical site, and while skewering and positioning the tissues to be joined onto needle 10, the retainer holder member is retracted within the device, thus affording the surgeon a clear line of sight to the needle to facilitate skewering and positioning of the tissues. When the tissues are in proper position, the needle holder member 102 is returned to its home position. The home position is the position of needle 10 and needle holder member 102 required for applying the retainer 30 to the needle 10. Preferably, this position may be positively identified by a detent mechanism on thumbwheel 74. In its retracted position, a top portion of retainer holder member 112 lies in contact with an edge 126 of working end 62. In order to locate a retainer 30 on top of needle 10, slide 76 is actuated to move drive rod 82 distally. Distal movement of drive rod 82 moves retainer holder member 112 distally, which in turn moves carriage 114 distally. Once retainer holder member 112 clears the edge 126, the biasing force of spring 116 moves carriage 114 distally with respect to retainer holder member 112, and rotates retainer holder member 112 counterclockwise to a position of the retainer holder member shown in phantom at 112' on FIG. 8B. Continued distal motion of drive rod 82 moves retainer holder member 112 distally until pin 118 contacts end 129 of slot 124. Further distal motion of drive rod 82 then causes clockwise rotation of the retainer holder member 112 about pin 118.

FIGS. 9A and 9B further illustrate details of a preferred embodiment of retainer holder member 112. Retainer holder member 112 may comprise a pair of parallel arms 130, spaced apart so as to accept retainer 30 therebetween. A distal end of arms 130 may include shallow notches or grooves 132 for frictionally engaging opposite sides of retainer 30, and ends of those notches or grooves may provide surfaces against which to position the retainer for proper application. A detent (not shown) could also be provided for positively positioning retainer 30 in retainer holder member 112. It is also preferred that dimensions of retainer holder member 112 are such that juxtaposed surfaces of notches 132 are spaced apart at a distance slightly smaller than the corresponding width of retainer 30. Thus, inserting a retainer between arms 130 causes them to be spread apart slightly, increasing the forces holding retainer 30 in retainer holder member 112. However, these contact forces are preferably sufficiently small so that, after retainer 30 is applied onto needle 10, retainer 30 is removed from retainer holder member 112 simply by a surgeon operating slide 76 to retract the retainer holder member 112 back into working end 62 of the instrument.

As indicated above, clockwise rotation of the retainer holder member 112 causes the retainer 30 to be passed over tip 16 of needle 10. Guided by visual indications, such as markings on the shaft of needle 10, and by tactile feedback to the drive rod 82 and slide 76, a surgeon continues to manipulate slide 76 until retainer holder member 112 is brought to a position 112" shown in phantom on FIG. 8B. In this position, the retainer 30 is properly positioned with respect to the needle holder member 102.

The fastener 32 and instrument 60 give the surgeon control over the positioning of the retainer relative to the base of the needle, and therefore the degree of compression applied to the tissues (or to a graft and artery) between the base of the needle on one side and the retainer on the other. This is similar to the manner in which a surgeon controls tension on tissues with conventional sutures and knottying techniques. As the surgeon seats the retainer down onto the shaft of the needle, the surgeon may control the degree of compression of the tissues based on both observing the tissues and the tactile feedback the surgeon receives through the control for moving the retainer support member in the handle of the instrument. This design permits the surgeon to take advantage of the training and experience gained in using conventional sutures and suturing techniques. The instrument may also be adapted to prevent the surgeon from applying the retainer beyond a pre-determined position on the shaft of the needle, for example, by providing a restraint to prevent the retainer holder member from closing beyond a pre-selected point. Alternatively or additionally, the instrument may also be adapted to prevent a surgeon from applying the retainer with a force that exceeds a predetermined limit, so as to prevent too much pressure from being exerted on the tissues held between the base of the needle and the retainer. This may for example be accomplished by the force limiter described above, or by another pressure regulating device provided between the control and the retainer holder member closing assembly. Furthermore, the instrument of the invention could include a pressure regulating device to apply a pre-selected amount of force to automatically close the retainer support member over the needle, and apply the retainer.

As would be appreciated by those skilled in the art, the relative positions of the needle holder member and the retainer holder member may be reversed in an alternative embodiment. In such an embodiment, after the tissues are skewered on the needle as described above, the retainer is held stationary, and the needle is brought down through the aperture of the retainer.

In the embodiment of the invention including a needle 202 and washer 208 as shown in FIGS. 5B–5D, it is understood that the retainer holder member 112 may be modified to hold washer 208. Thereafter, once the washer 208 is positioned on needle 202, a deforming member (not shown) may come down to deform the needle shaft 206 as described above. The deforming member may be pivotally mounted on the retainer holder member, or as a separate mechanism, and may be controllably actuated by controls in the handle end of the instrument. Alternatively, the deforming member may be part of a separate tool that is used to the deform the shaft 206 once the retainer holder member 112 has positioned the washer 208 in its proper position over needle 202.

Needle holder assembly 100 in working end 62 further includes a clip 140 as shown in FIG. 10. Clip 140 is slidably mounted to the upper surface of needle holder member 102, such that clip 140 can translate distally and proximally between position 140 and position 140', shown in phantom in FIG. 10. Clip 140, mounted to the needle holder member 102, remains in a stationary position relative to the needle holder member 102 throughout the holder's range of motion about axle 103.

In preparation for use, base 12 of a needle 10 is inserted into hole, or recess, 155 in needle holder member 102. As previously described, hole 155 in the needle holder member 102 is in part defined by flat surfaces 156 which are provided to engage counterpart surfaces 26 of the base 12 of the needle (FIGS. 1A and 1B) to assist in keeping the needle in a substantially constant and predetermined orientation relative to the needle support member 102. The front of clip 140 includes fingers 140b and 140c designed to engage detent 24 (FIGS. 1A and 1B) when the clip is in a position 140' to thereby lock the needle in place on the needle holder member. If a needle shown in FIGS. 1C or 1D were used, the flat surfaces of the hole or recess in needle holder 102 would be oriented differently and would be arranged to engage surfaces 28 of the base of the needle.

Clip 140 is coupled via a flexible wire 146 and slide 148 (explained hereinafter) to drive rod 84, which drive rod 84 is in turn coupled to a slide 78 in the handle end 64 of the instrument (FIG. 7). Distal actuation of slide 78 moves drive rod 84 distally until an end 147 of drive rod 84 contacts an end 140a of clip 140. Upon continued actuation of slide 78, end 147 of drive rod 84 pushes clip 140 distally until fingers 140b and 140c lock the needle 10 in place on needle holder member 102.

After the pinned retainer fastener has been formed, it is necessary to release the fastener and remove the instrument from the surgical site. Towards this end, the distal portion of drive rod 84 includes a bore hole 84*a* in which is mounted slide 148 attached to flexible wire 146. Wire 146 is in turn affixed to clip 140. Bore hole 84*a* further includes a slot 152 longitudinally formed through the outer wall of bore hole 84*a*. A pin 150 affixed to slide 148 rides within slot 152. Upon moving slide 78 in the proximal direction, drive rod 84 is moved proximally. Clip 140, wire 146 and slide 148 remain stationary during proximal movement of drive rod 84 until a distal edge of slot 152 engages pin 150 whereupon pin 150, slide 148, wire 146 and the clip 140 are pulled proximally with the drive rod 84. The wire 146 and slide 148 allow clip 140 to pivot with needle holder member 102 without relative movement between the clip and needle holder member, and without exerting a force on drive rod 84 or slide 78. As would be appreciated by those skilled in the art, clip 140 may be attached to drive rod 84 by mechanisms other than wire 146 and slide 148 in alternative embodiments of the invention. Upon proximal movement of clip 140, fingers 140*b* and 140*c* disengage from base 12, thereby releasing the fastener 32 from the instrument 60.

After a surgical fastener is applied using instrument 60 as described above, tip 16 of needle 10 is removed (either before or after release of the fastener 32 from the instrument 60) so that it does not injure surrounding tissues. If tip 16 and shaft 14 are swedged together, as illustrated in FIG. 1D, a suitable grasping tool may be used to simply remove tip 16 from shaft 14, leaving only a blunt end of shaft 14 exposed. In an alternative embodiment of the instrument 60, the instrument may include a needle removal member in the distal end, which member is operated by controls in the handle end of the instrument. The function of the needle removal member is to grasp and remove the tip 16 of a two-part needle, after the retainer is applied to the retainer-engaging portion of the needle. Details relating to such a needle removal member are disclosed in U.S. patent application Ser. No. 08/781,579, previously incorporated herein by reference. As would be appreciated by those skilled in the art, such a needle removal member may alternatively be combined with the retainer holder member 112 so as to remove the needle tip 16 after the retainer has been applied to the needle.

In embodiments of the invention where shaft 14 and tip 16 comprise an integral piece, a suitable tool may be used to cut or otherwise trim tip 16 from needle 10. A trimming tool 160 is shown in FIGS. 11A and 11B. This tool comprises trimming assembly 162 and handle assembly 165 disposed, respectively, at a distal and a proximal end of shaft 166. Trimming assembly 162 comprises fixed blade 168 and sliding blade 170 juxtaposed in an edge-to-edge relation adjacent to guide 172. Handling assembly 165 comprises lever 174 coupled to a suitable mechanism for driving sliding blade 170. For example, in FIG. 11, sliding blade 170 is coupled to drive link 176 which extends the length of shaft 166. Rack gear 178 disposed at a proximal end of shaft 166 is engaged by pinion gear 180. Lever 174 is coupled to pinion gear 180, whereby operation of lever 174 causes rotation of pinion gear 180 resulting translational motion of sliding blade 170. Spring 182 biases drive link 176 so that sliding blade 170 is retracted away from fixed blade 168 absent actuation of lever 174.

Trimming tool 160 is introduced into the patient's body through a cannula and manipulated by a surgeon so that tip 16 of needle 10 travels through guide 172 and is secured in grip pad 173. Grip pad 173 may be made of any material that may be penetrated by tip 16, such as silicone. The opening in guide 172 is sized so that retainer 30 fits within the opening while preventing retainer 30 from extending beyond a cutting plane defined by fixed blade 168 and sliding blade 170. Actuating the blades of trimming tool 160 cut tip 16 substantially flush with retainer 30. When retainer 30 has a soft elastomeric cap (see FIG. 2A), guide 172 may position retainer 30 so that a thin portion of the outer covering is also trimmed off by action of blades 170 and 168. The surgeon may also depress a soft elastomeric cap, trim the tip off, and allow the cap to elastically return to its original shape and extend beyond the end of the trimmed needle shaft, thereby more effectively covering the shaft.

After positioning retainer 30 in guide 172, the surgeon actuates lever 174 thereby moving sliding blade 170 toward fixed blade 168. Tip 16, being positioned between the sliding and fixed blades is sheared off, cut, or otherwise removed from needle 10. Tip remains secured in grip pad 173 and is removed from the patient's body when trimming tool 160 is withdrawn. Trimmed tip 16 may then be removed from trimming tool 160 and the procedure repeated for each surgical fastener. Depending on various aspects of a particular surgical procedure, a surgeon may trim each fastener immediately after each is applied, after all the fasteners have been applied, or in some other sequence.

The instrument 60 for applying the fastener 32 may be formed by constructing the controls in handle end 64, attaching the drive rods to the controls at the handle end, and affixing the assemblies in the working end 62 to the drive rods and to the support member 63. Thereafter, the support member 63 may be inserted in the distal end of shaft 72 and affixed by suitable means. Alternatively, working end 62 may be designed to accept the various assemblies directly, without using support member 63.

Up to this point, the assemblies in the working end have been described as being actuated and controlled by manually operated thumbwheels and slides in the handle end of the instrument. However, in alternative embodiments of the invention, it is understood that formation of the pinned retainer and its release from the applier may be automated by driving the drive rods and distal mechanisms of the instrument through their ranges of motion by motors, actuators, pneumatic or hydraulic systems, or some other force transmission mechanism instead of or in addition to the manual actuation of the drive rods and distal mechanisms as described above. In such an embodiment, the motors, actuators and/or other force transmission mechanisms may be activated by known, manually activated switches or buttons in the handle end of the instrument. As would be appreciated by those skilled in the art, actuation of the drive rods to affect the motions of the various assemblies in the working end as described above may be accomplished by affixing the proximal ends of the drive rods to the motors, actuators and/or force transmission mechanisms to bring about the desired controlled movement of the drive rods and working end assemblies and therefore automate these functions. Additionally, force limiters may be provided to limit the force with which the motors and/or actuators drive the drive rods and tube. The force limiters may be mechanical, such as of the type described above, or the force limiters may be electrical, such as closed loop feedback signals which monitor the amount of force exerted on the drive rods and/or distal end assemblies.

In a further embodiment of the present invention, it is contemplated that the manually operated mechanisms in the handle end may be omitted, and the assemblies in the working end of the instrument may be actuated and controlled by a surgical robot, to which shaft 72, and the assemblies and mechanisms contained therein, are attached.

In such an embodiment, motors, actuators, pneumatic/ hydraulic systems and/or other force transmission mechanisms may be provided as described above for driving the drive rods and assemblies in the working end of the instrument for forming and releasing a pinned retainer. The motors, actuators and/or other force transmission mechanisms may in turn be controlled remotely by a computer and/or a surgeon.

This invention also supplies a method of attaching soft tissues together in the chest, abdominal cavity or retroperitoneal space, and for attaching a graft to an artery in these areas. This invention is particularly useful for minimally invasive surgical procedures, especially for performing an anastomosis between a vascular graft and an artery. The method is applicable to arteries from 1–2 millimeters in diameter (such as coronary arteries), and to larger arteries (such as the aorta, iliac arteries, and femoral arteries).

The method uses the instrument of the invention containing at least one needle and one retainer to apply a two-part surgical fastener of the invention. A small incision is made in the patient's abdominal cavity, chest, or retroperitoneal space, depending on the clinical situation, and the distal or working end of the shaft of the instrument is inserted through this opening. In carrying out a vascular anastomosis, the surgeon preferably first inserts the tip of the needle through the exterior wall of a graft. The tip of the needle is then inserted through the interior lumen of the artery and through the arterial wall at the appropriate location. If the artery is heavily calcified, the surgeon may make a hole in the arterial wall using a punch or other device, before inserting a blunt tipped needle through the arterial wall. Once the needle is in place, through both the graft and the arterial wall, the surgeon employs the instrument to move the retainer onto the shaft of the needle. By controlling the movement of the retainer, the surgeon places the retainer on the shaft at a selected position. The retainer securely engages to the shaft of the needle. This permanently secures the graft and the arterial wall together between the base of the needle and the retainer. This method results in the anastomotic edges of the graft and artery being substantially everted, and both shaft and retainer lying in an extra-luminal position. This procedure, therefore, isolates the intra-luminal area from coming in contact with a fastener. As described above, the retainer and the base of the needle are designed so the surfaces in contact with the artery on one side and the graft on the other are sufficient to spread the forces of contact enough to ensure viability of the artery, while providing a hemostatic seal between graft and artery. Those surfaces are also sufficiently large to prevent migration of the fastener through the graft or the artery after application. After a fastener is in proper position through the graft and artery, with the retainer in proper location, the tip of the needle may be trimmed or cut off. Alternatively, as explained above, if the tip has been "swedged on", the tip may be separated from the shaft by grasping the tip and separating it from the shaft. This can be accomplished either by a separate grasping tool to remove the needle tip, or by a mechanism built into the applying instrument. The same method may be employed to join other soft tissues.

The method may involve repeating these steps to apply a series of additional fasteners. These steps may be repeated with additional fasteners being applied around the anastomotic lumen, until the artery and graft have been joined together in a substantially hemostatic relationship. The number of fasteners will vary with the size of the artery and the circumference of the anastomosis. Typically, between about 8 and about 25 fasteners may be used for a typical end-to-end anastomosis between the aorta and a vascular graft. The method may also be used in conjunction with other surgical fasteners, such as staples or vascular clips, or with conventional sutures, to provide a hemostatic anastomosis. This method is useful in end-to-end, side-to-end, and side-to-side procedures. In the construction of a vascular anastomosis, these fasteners are applied at positions and locations substantially identical to those used for conventional sutures, and suturing techniques. Hence, the fasteners may be applied to within about 0.5 millimeters to about 5 millimeters from the cut edge of the arterial wall, and within no less than 3 threads of the cut end of a prosthetic, woven graft.

The method of vascular grafting using this present invention may be illustrated in the context of an endoscopic aortobifemoral bypass procedure. The patient is positioned on the operating room table midway between a right lateral decubitus position and a supine position, resulting in availability of the left flank and both groins to be sterilely prepared for operation. The table is slightly flexed to open the iliac crest-costophrenic angle. A standard sterile preparation of the patient is performed. Standard draping technique is accomplished. Standard vertical groin incisions are made to mobilize the common femoral, superficial femoral, and profunda femoral arteries in each groin. By finger dissection, a tunnel toward the abdomen is made from each incision by palpation along the course of the common femoral artery just superior to the common femoral artery and just below the inguinal ligament. The tunnel is extended as far as a finger can palpate.

Along the mid axillary line as drawn to the iliac crest midway between the iliac crest and the ribs a small incision is made in the skin and subcutaneous tissue. Utilizing finger dissection, dissection is carried down through the fat to the posterior muscles. A balloon dissector is then placed through this small incision at this location and a cavity created. When the balloon dissector has created a cavity in the potential space between the retroperitoneal fat and the psoas muscle, then the cavity is further expanded by placing a sealed port and insulating $CO_2$. Once insufflating has been accomplished, the space is examined and a correct relationship between the lateral and anterior abdominal walls is established so then in the centermost portion of the roof of the cavity a port is made to insert a lifting device. The dissection continues without further $CO_2$ insufflation.

Several small incisions are made in the abdominal wall to carefully position abdominal wall retractors which are attached to the lifting device. With the space now developed and the aorta exposed from the renal vein to the bifurcation and the left iliac artery exposed to the left hypogastric artery, further dissection is accomplished superiorly around the aorta and each of the lumbar vessels and also just above the right common iliac artery. Care is again taken to ensure not entering the peritoneal cavity. The aorta is completely dissected free just below the renal arteries which are identified visually, and each of the lumbar vessels is controlled with temporary clips. The quality of the pulse in the aorta is confirmed by comparison with preoperative angiograms to ensure that the correct area for anastomosis of the bypass graft has been obtained and that the aorta is soft and pliable and will accept surgical fasteners. Dissection is then completed to both groins and the tunnels that were started in each groin is noted to be complete by passing a tunneler from the groin along the previously palpated space of the iliac artery to the retroperitoneal cavity (created by the primary dissection of the aorta).

A correctly sized graft is then selected and fashioned to ensure that the bifurcation length is appropriate, and the proximal end is trimmed for either an end-to-end or end-to-side anastomosis. The graft is then introduced through a port into the dissected space and each of the limbs are appropriately positioned in the groins where they will ultimately be attached. An appropriate aortic clamp is selected to clamp the aorta just below the renal arteries, and another clamp is selected for clamping the aorta at the level of the inferior mesenteric artery. The aorta is cross-clamped. clamped. Ischemia time begins at this point and the operation is directed to be done as expeditiously as possible.

If an end-to-end anastomosis is planned, then the aorta is divided and excess aorta is removed to permit exposure of the end of the infra renal aorta. The graft which has been previously positioned is then held by graspers, and the system of the invention is utilized to attach the graft to the aorta. Each fastener is placed in turn at appropriate spacing to ensure correct sealing of the graft to the aorta. After all fasteners have been placed and secured, a clamp that may grasp either limb of the graft is applied to the limbs of the graft, and the aorta clamp is temporarily opened to distend the graft with normal pulsatile arterial flow. Upon noting a secure anastomosis, the proximal aortic clamp is removed, however if any leak points are noted another fastener is applied or sewn into place positioned to close the bleeding point.

When hemostasis is secure, the left limb of the graft is passed though the tunnel by grasping it with a grasper from the groin incision and the graft is delivered into the groin wound. A standard end of graft to side of common femoral or profunda femoris artery is performed. A similar process is utilized for the right groin. Each graft limb in turn is opened to flow upon satisfactory completion of the anastomosis. The fasteners are used to sew closed the stump of the distal aorta. Areas are inspected to ensure adequate hemostasis, and when this is ensured, wounds are irrigated with antibiotic solution. The retroperitoneal cavity is then allowed to collapse upon the newly placed graft. No closure of this cavity is required as the ports and laprolift are removed. Laparoscopic wounds are then closed in standard fashion ensuring absorbable sutures close the small fascial defects and the skin wounds are steri-stripped. The open groin wounds are then closed in standard fashion utilizing three layers for closure of each wound and the skin edges are approximated with staples.

It is to be understood that the embodiments shown as described above are only illustrative of the principles of the invention, and various modifications can be made by those skilled in the art without departing from the scope and spirit of the invention. The skilled artisan will also appreciate that the present invention can be practiced by other than the described embodiments, which are provided for purposes of illustration and not of limitation, and that the present invention is only limited by the claims that follow.

We claim:

1. A surgical fastener comprising:
   a needle including a base, a shaft and a tip, said base comprising an upper surface, a lower surface, and further comprising at least two substantially planar surfaces extending in substantially the same direction, said shaft extending from the upper surface of said base and having a retainer-engaging portion, and said tip being at an end of said shaft opposite said base and configured to pierce a graft, artery or other soft tissue, and
   a retainer comprising a plate comprising resilient material, said plate having an aperture defined by a portion of said plate that is adapted to engage said shaft and having means for securing the retainer at a selectable position on the retainer-engaging portion of said shaft of the needle without substantially deforming said shaft, said retainer further having a surface that cooperates with the upper surface of the base of the needle to contact and secure between those surface portions of materials together wherein at least one of the portions is tissue.

2. The fastener of claim 1 wherein the fastener has a closed state where the shaft of the needle is within the aperture of the retainer plate which is deformed by the shaft of the needle, said deformation providing a contact force to hold the retainer in place.

3. The surgical fastener of claim 1 wherein said base includes a flange and said at least two substantial planar surfaces are formed in said flange.

4. The surgical fastener of claim 1 wherein said base includes at least one slot and said at least two substantial planar surfaces are formed along said at least one slot.

5. The surgical fastener of claim 1 wherein said base includes two slots with each one of the at least two substantial planar surfaces forming a portion of one of the two slots.

6. The surgical fastener of claim 1 wherein transverse cross-section of the shaft varies along the longitudinal axis of the shaft.

7. The surgical fastener of claim 1 wherein said shaft is curved.

8. The surgical fastener of claim 7 wherein said shaft is curved along its entire length.

9. The surgical fastener of claim 1 wherein the retainer-engaging portion of the shaft comprises one or more ridges.

10. The surgical fastener of claim 1 wherein the retainer-engaging portion of the shaft comprises one or more detents located at predetermined locations on the retainer-engaging portion of the shaft.

11. The surgical fastener of claim 1 wherein the retainer-engaging portion of the shaft comprises a textured surface.

12. The surgical fastener of claim 1 wherein said upper surface of the base is substantially planar.

13. The surgical fastener of claim 1 further comprises a circumferential groove formed in the base.

14. A method for attaching soft tissues located in the abdominal cavity, chest or retroperitoneal space and for attaching a graft to an artery in these areas with a surgical fastener comprising,
   providing an instrument having an elongated shaft with a distal end portion for applying a surgical fastener,
   providing only one needle to a needle holder member and at least one retainer to a retainer holder member at the distal end of the instrument,
   incising a patient's tissues to create at least one opening into the patient's abdominal cavity, chest or retroperitoneal space,
   inserting the distal end of the shaft of the instrument through the opening so that the distal end is disposed in the patient,
   passing the shaft of the needle through a portion of one tissue, graft or artery and through a second tissue, artery or graft, and
   actuating a closing assembly associated with the retainer holder member to place the retainer on the needle and form a surgical fastener.

15. The method defined in claim 14 wherein the method further comprises releasing the needle from the instrument.

16. The method defined in claim 14 wherein the passing and actuating steps are repeated to apply additional fasteners.

17. The method defined in claim 14 wherein the method further comprises removing an end portion of the needle after a fastener have been applied.

18. The method defined in claim 14 wherein the incising step creates a small incision and wherein the inserting, passing and actuating steps are performed by minimally invasive surgical procedures.

19. The method defined in claim 14 wherein a shaft of the needle is passed through a portion of a graft or artery and through a portion of an artery or graft to form a portion of an artery-to-graft anastomosis.

20. The method defined in claim 14 wherein the artery is selected from the group consisting of the aorta, the coronary arteries, the iliac arteries and the femoral arteries.

21. The method defined in claim 14 wherein the artery is at least about 2 mm diameter or larger.

22. A surgical fastening system, comprising:
   a needle consisting of a base and a body member, said base comprising an upper surface, a lower surface, and further comprising at least two substantially planar surfaces extending in substantially same direction, said body member having a first end affixed to said base, and a second end opposite said first end, said second end being capable of passing through tissues, or tissue and graft;
   a retainer comprising a plate comprising resilient material, said plate having an aperture adapted to engage said shaft and having means for securing the retainer at a selectable position on the shaft of the needle without substantially deforming said shaft, said retainer further having a surface that cooperates with the upper surface of the base of the needle to contact and secure between those surface portions of materials together wherein at least one of the portions is tissue; and
   an instrument having a portion adapted to be slideably received by the at least two substantial planar surfaces of the base of the needle so that the needle may be manipulated to skewer materials without rotation.

23. A surgical fastener system as recited in claim 22, further comprising manual controls for controlling said instrument.

24. A surgical fastener system as recited in claim 22, further comprising automated robotic controls for controlling said instrument.

25. A surgical retainer system for fastening together tissues, or tissue and graft, comprising:
   a retainer including an aperture; and an instrument, including:
   a shaft having a proximal and distal end,
   a needle removably affixed to said distal end,
   first means in said distal end for articulating said needle to skewer a first tissue or graft, align the first tissue or graft to a desired position with respect to a second tissue or graft, and skewer the second tissue or graft in the desired position with respect to the first tissue or graft, and
   second means for holding said retainer, said second means capable of moving between a first position where said second means and said retainer are retracted proximally into said shaft to provide a clear line of sight of a surgeon to the first means and needle, and a second position where said second means is capable of positioning said retainer over said needle.

26. A surgical retainer system for fastening together tissues, or tissue and graft, as recited in claim 25, further comprising third means for removing an end portion of said needle.

27. A surgical retainer system for fastening together tissues, or tissue and graft, comprising:
   a needle including a base, a shaft affixed to said base, said shaft having a retainer-engaging portion, and an end capable of passing through the tissue, or tissue and graft; and
   a retainer including an aperture for allowing said retainer to fit over said needle onto said retainer-engaging portion;
   wherein said retainer includes a metallic base, and an elastomeric cap affixed to said base.

28. A surgical instrument for fastening together tissues, or tissue and graft, together, comprising:
   a shaft including a distal end and a proximal end opposite said distal end;
   a needle holder in said distal end for holding a needle;
   first means in said distal end for articulating said needle holder to allow said needle to skewer the tissues, or tissue and graft, and to align the tissues, or tissue and graft with respect to each other;
   a retainer holder in said distal end for holding a retainer;
   second means in said distal end for moving said retainer holder between a first position where said retainer holder is retracted proximally to provide a clear line of sight of a surgeon to the needle holder and first means, and a second position where said retainer holder is capable of locating a retainer over a needle held by said needle holder; and
   controls located remote from said distal end for controlling operation of said first means and said second means.

29. A surgical instrument for fastening tissues, or tissue and graft, together as recited in claim 28, wherein said controls comprise hand-actuated controls.

30. A surgical instrument for fastening tissues, or tissue and graft, together as recited in claim 28, wherein said controls comprise automated robotic controls.

31. A surgical instrument for fastening tissues, or tissue and graft, together as recited in claim 28, further comprising connecting means for connecting said controls to said first and second means.

32. A surgical instrument for fastening tissues, or tissue and graft, together as recited in claim 31, wherein said controls and said connecting means together comprise an automated robotic system for actuating said first means and said second means.

33. A surgical instrument for fastening tissues, or tissue and graft, together as recited in claim 31, further comprising a motor, controlled by said controls, for actuating said connecting means.

34. A surgical instrument for fastening tissues, or tissue and graft, together as recited in claim 31, further comprising pneumatic means, controlled by said controls, for actuating said connecting means.

35. A surgical instrument for fastening tissues, or tissue and graft, together as recited in claim 31, further comprising hydraulic means, controlled by said controls, for actuating said connecting means.

36. A method of fastening together tissues, or tissue and graft, in a surgical procedure, comprising the steps of:
    (a) skewering the tissues, or tissue and graft, onto a needle having a base in a minimally invasive procedure;
    (b) positioning a retainer over the needle in a minimally invasive procedure to fasten the tissues, or tissue and graft together between the needle base and retainer; and
    (c) providing a clear line of sight for a surgeon to the needle during said step (a) by positioning the retainer out of the line of sight.

37. A surgical fastener comprising:
    a needle including a base, a shaft and a tip, said base having an upper surface, a lower surface, and means for preventing needle rotation when mounted in a needle holder, said shaft extending from said upper surface of the base and having a retainer-engaging portion, and said tip being at an end of said shaft opposite said base and configured to pierce a graft, an artery or other soft tissues, and
    a retainer comprising a plate comprising resilient material, said plate having an aperture which has means for frictionally engaging said shaft and secure the retainer at a selectable position on the said retainer-engaging portion of the shaft without substantially deforming said shaft, said retainer further having a surface that cooperates with the upper surface of the base of the needle to contact and secure between those surface portions of materials together wherein at least one of the portions is tissue.

* * * * *